US009180235B2

(12) United States Patent
Forsell

(10) Patent No.: US 9,180,235 B2
(45) Date of Patent: Nov. 10, 2015

(54) HEART HELP PUMP, SYSTEM AND METHOD

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/123,231

(22) PCT Filed: Oct. 12, 2009

(86) PCT No.: PCT/SE2009/000445
§ 371 (c)(1),
(2), (4) Date: Apr. 7, 2011

(87) PCT Pub. No.: WO2010/042008
PCT Pub. Date: Apr. 15, 2010

(65) Prior Publication Data
US 2011/0201870 A1   Aug. 18, 2011

Related U.S. Application Data

(60) Provisional application No. 61/202,381, filed on Feb. 24, 2009.

(30) Foreign Application Priority Data

Oct. 10, 2008 (SE) ...................................... 0802161

(51) Int. Cl.
*A61N 1/362* (2006.01)
*F04B 35/00* (2006.01)
*A61M 1/10* (2006.01)
(Continued)

(52) U.S. Cl.
CPC .................. *A61M 1/101* (2013.01); *A61F 2/01* (2013.01); *A61M 1/1015* (2014.02); *A61M 1/1031* (2014.02); *A61M 1/1036* (2014.02);
(Continued)

(58) Field of Classification Search
CPC ... A61M 1/122; A61M 1/101; A61M 1/1031; A61M 1/125; A61M 1/1036; A61N 1/3627
USPC .......................................... 600/16–17; 623/3
See application file for complete search history.

(56) References Cited

U.S. PATENT DOCUMENTS 4,304,225 A    12/1981   Freeman
4,688,998 A *  8/1987   Olsen et al. .................... 417/356
(Continued)

FOREIGN PATENT DOCUMENTS

EP    0378251    7/1990
GB    885 674    12/1961
(Continued)

OTHER PUBLICATIONS

International Search Report for PCT/SE2009/000445, mailed Dec. 15, 2009.
(Continued)

*Primary Examiner* — Michael Kahelin
*Assistant Examiner* — Minh Duc Pham

(57) ABSTRACT

The present invention relates to a heart pump apparatus comprising a turbine pump for assisting the heart of a human patient. The invention is based on the realization that a turbine without a center axis would improve the capacity of the heart help pump apparatus. The present invention also relates to a turbine pump system for assisting the heart of a human patient. The present invention also relates to operation methods and methods for surgically placing a rotating body of a turbine pump and a stator of a turbine pump in a patient.

24 Claims, 38 Drawing Sheets

(51) Int. Cl.
*A61F 2/01* (2006.01)
*A61M 1/12* (2006.01)

(52) U.S. Cl.
CPC .............. *A61M 1/122* (2014.02); *A61M 1/125* (2014.02); *A61F 2230/005* (2013.01); *A61M 1/127* (2013.01)

(56) References Cited

U.S. PATENT DOCUMENTS

| | | | |
|---|---|---|---|
| 5,112,202 A | | 5/1992 | Oshima et al. |
| 5,211,546 A | * | 5/1993 | Isaacson et al. ............... 417/356 |
| 6,149,683 A | * | 11/2000 | Lancisi et al. .................. 623/3.1 |
| 6,302,661 B1 | * | 10/2001 | Khanwilkar et al. ....... 417/423.7 |
| 6,527,521 B2 | * | 3/2003 | Noda ............................ 417/355 |
| 2002/0165575 A1 | * | 11/2002 | Saleh ............................ 606/200 |
| 2003/0233143 A1 | | 12/2003 | Gharib et al. |
| 2010/0076247 A1 | * | 3/2010 | Zilbershlag et al. ............ 600/17 |
| 2011/0196192 A1 | | 8/2011 | Forsell |
| 2011/0196193 A1 | | 8/2011 | Forsell |
| 2011/0196483 A1 | | 8/2011 | Forsell |
| 2011/0196484 A1 | | 8/2011 | Forsell |
| 2011/0196485 A1 | | 8/2011 | Forsell |
| 2011/0196486 A1 | | 8/2011 | Forsell |
| 2011/0201871 A1 | | 8/2011 | Forsell |
| 2011/0202131 A1 | | 8/2011 | Forsell |
| 2011/0224787 A1 | | 9/2011 | Forsell |

FOREIGN PATENT DOCUMENTS

| | | |
|---|---|---|
| WO | WO 01/12108 | 2/2001 |
| WO | WO 2004/101029 | 11/2004 |
| WO | WO 2008/135988 | 11/2008 |
| WO | WO 2009/010799 | 1/2009 |

OTHER PUBLICATIONS

Written Opinion of the International Searching Authority for PCT/SE2009/000445, mailed Dec. 15, 2009.
U.S. Appl. No. 13/123,232 (Forsell), filed Apr. 7, 2011.
U.S. Appl. No. 13/123,255 (Forsell), filed Apr. 8, 2011.
U.S. Appl. No. 13/123,284 (Forsell), filed Apr. 8, 2011.
U.S. Appl. No. 13/123,394 (Forsell), filed Apr. 8, 2011.
U.S. Appl. No. 13/123,402 (Forsell), filed Apr. 8, 2011.
U.S. Appl. No. 13/123,436 (Forsell), filed Apr. 8, 2011.
U.S. Appl. No. 13/123,446 (Forsell), filed Apr. 8, 2011.
U.S. Appl. No. 13/123,586 (Forsell), filed Apr. 11, 2011.
U.S. Appl. No. 13/123,587 (Forsell), filed Apr. 11, 2011.

* cited by examiner

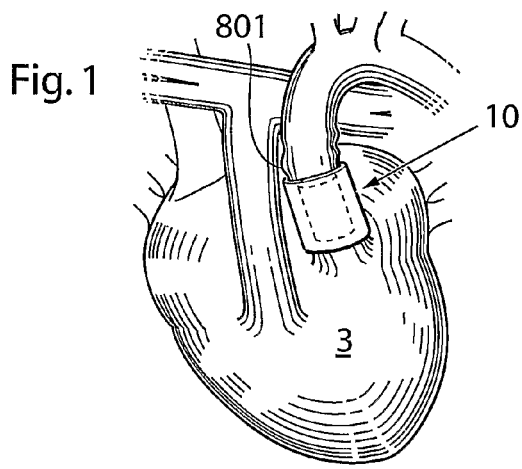
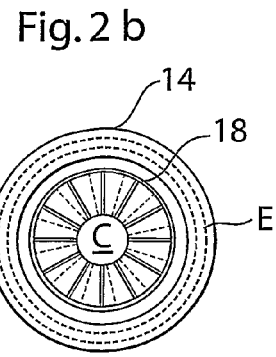
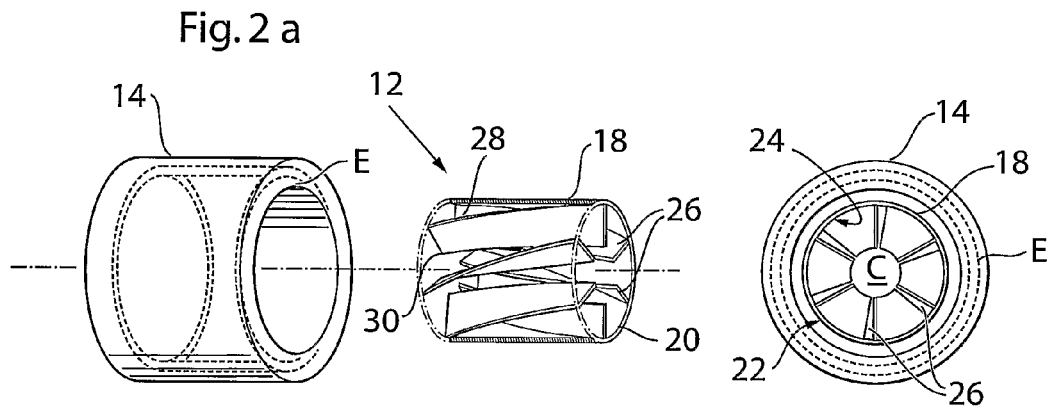
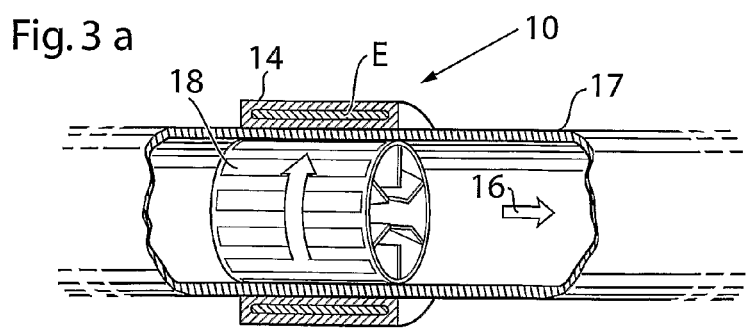
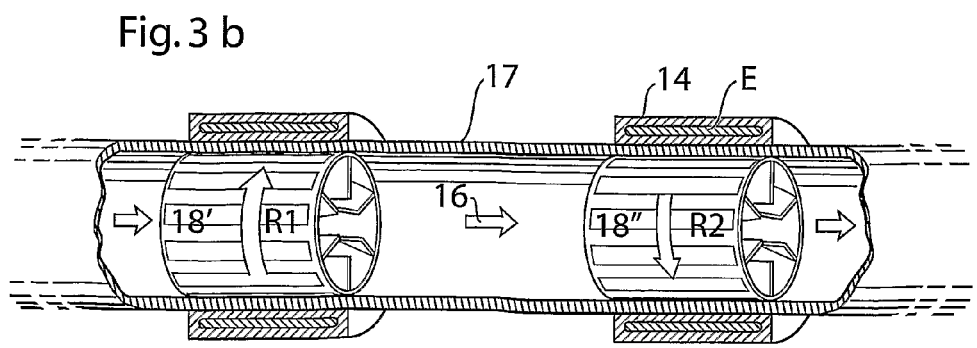

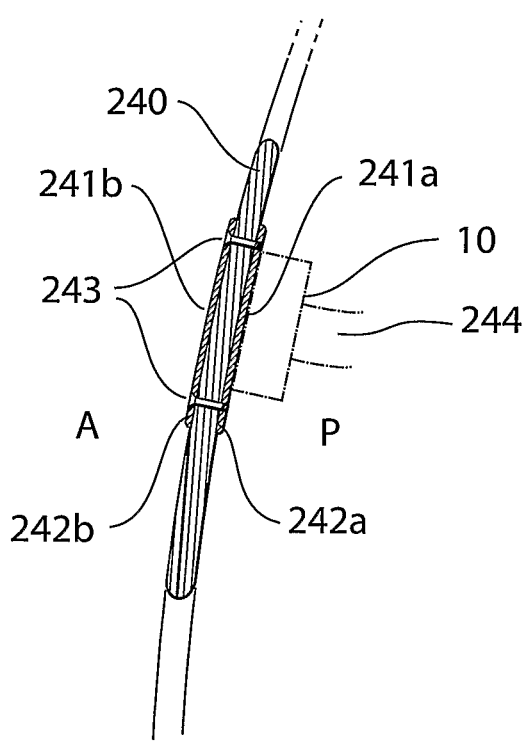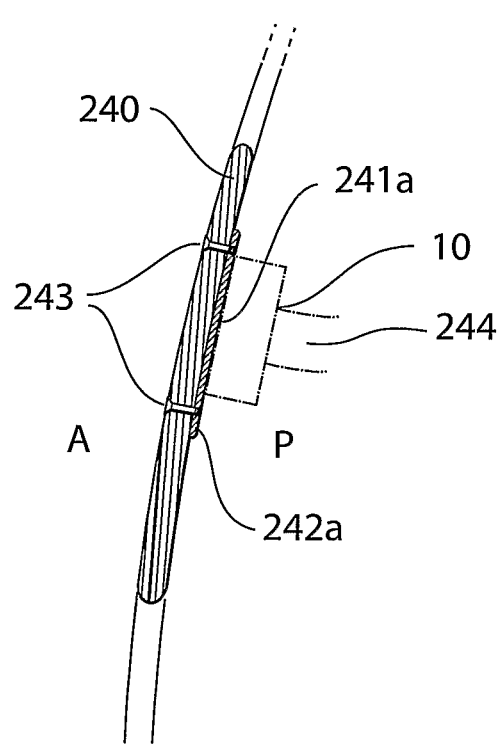

Fig.58

1. Inserting a needle or a tube like instrument into the abdomen of the patient's body, 2. Using the needle or a tube like instrument to fill the abdomen with gas thereby expanding the abdominal cavity, 3. Placing at least two laparoscopic trocars in the patient's body, 4. Inserting a camera through one of the laparoscopic trocars into the abdomen, 5. Inserting a dissecting tool through one of said laparoscopic trocars and dissecting an intended placement area, 6. Placing the rotating body in any part of the blood stream in the abdominal aorta, and 7. Connecting a source of energy for powering the device.

Fig.60

1. Inserting a needle or a tube like instrument into the thorax of the patient's body, 2. Using the needle or a tube like instrument to fill the thorax with gas thereby expanding the thoracic cavity, 3. Placing at least two laparoscopic trocars in the patient's body, 4. Inserting a camera through one of the laparoscopic trocars into the thorax, 5. Inserting at least one dissecting tool through one of said at least two laparoscopic trocars and dissecting an intended placement area in the vascular system of the patient, 6. Placing the rotating body in any part of the blood stream in the thorax, inside a blood stream of the blood vessel in the heart, or the aorta or inside the pulmonary artery of the patient, 7. Placing a stator in the placement area, outside the blood stream of the blood vessel, outside the heart, or the aorta or outside the pulmonary artery of the patient, placing said stator on the outside of said rotating body, supplying wireless energy to said rotating body causing rotating movement of said rotating body and 8. Connecting a source of energy for powering said stator.

HEART HELP PUMP, SYSTEM AND METHOD

This application is the U.S. national phase of International Application No. PCT/SE2009/000445, filed 12 Oct. 2009, which designated the U.S. and claims priority to Swedish Application No. 0802161-0, filed on 10 Oct. 2008, and claims the benefit of U.S. Provisional No. 61/202,381, filed on 24 Feb. 2009, respectively, the entire contents of each of which are hereby incorporated by reference.

FIELD OF INVENTION

The present invention relates generally to a heart pump apparatus and a system for assisting the heart of a human patient and more particularly to a heart pump apparatus and a system that provide the human heart apparatus with additional pumping capacity. The invention also relates to a method of assisting the heart of a human patient.

BACKGROUND

There are prior art implanted heart help pumps which include a turbine. These heart help pumps are implanted either in a blood vessel or in a heart chamber. All these pumps have a centre axis about which turbine vanes are provided. These vanes propeller blood as the centre axis rotates, thus assisting the heart with the work of pumping blood through the blood vessel system of the patient.

SUMMARY OF THE INVENTION

One object with the present invention is to achieve a heart pump apparatus and a system for assisting the heart of a human patient that at least partially eliminates those drawbacks that are associated with devices according to the state of the art. Further, an object of the present invention is to provide an apparatus, a system, and a method for assisting the heart of a human patient that are uncomplicated in the design, and/or easy to produce, and/or simple to adapt to the heart of a human patient, and/or cost-efficient.

These objects have been reached with a heart pump apparatus comprising a turbine pump for assisting the heart of a human patient, according to the present invention as defined in the appended claim 1, and further reached with systems and methods according to the following independent claims.

The invention is based on the realization that a turbine without a centre axis would improve the capacity of the heart help pump apparatus.

One advantage is that the present invention may decrease the accumulation of fat in the heart. A further advantage with the present invention is that the turbulence of the flow of blood in the heart can be decreased. The turbine pump of the present invention is adapted to create a laminar flow.

According to a first aspect of the present invention there is provided a heart pump apparatus for assisting the heart of a human patient. The heart pump apparatus comprising a turbine pump, a part of which is adapted to be placed in a blood stream in the human patient to provide the heart of the human patient with additional pumping capacity. The turbine pump is a centre axis free turbine pump.

In one embodiment, the turbine pump comprises a rotating body and a stator. The rotating body is adapted to be placed in a blood stream. The stator is preferably adapted to be placed outside the blood stream and opposite the rotating body. The stator can be a part of an electrically controlled arrangement, which includes elements for receiving current to increase or decrease a magnetic field created at the stator, for providing rotation of the rotating body or not, by creating a magnetic field between the poles of the stator.

According to one embodiment, at least two rotating bodies can be implanted in sequence in the same blood vessel. If there are two rotating bodies in sequence, one can be adapted to rotate clockwise and the following other rotating body can be adapted to rotate counter clockwise, or vice versa.

The rotating body is provided with blades placed internally in the rotating body, the blades can be of different design and configuration.

The present invention also relates to a turbine pump system for assisting the heart of a human patient, comprising a heart pump apparatus according to claim 1. The system can comprise a rotating body adapted to be placed in said blood stream. Further, the system can comprise a stator adapted to be placed outside the blood vessel and opposite the rotating body.

The present invention also relates to a method, or an operation method, of surgically placing a rotating body of a turbine pump and a stator of a turbine pump, respectively, as described above, in a patient via a laparoscopic thoracic approach.

The present invention also relates to an operation method for surgically placing a rotating body of a turbine pump, as described above, in a patient.

The present invention also relates to an operation method for surgically placing a stator of a turbine pump, as described above, in a patient.

The present invention also relates to a method, or an operation method, of surgically placing a rotating body of a turbine pump and a stator of a turbine pump, respectively, in a patient via a laparoscopic abdominal approach.

The present invention also relates to a method according to any of the operation methods or methods of surgically placing a rotating body and/or a stator as mentioned above, wherein said energy source is using energy, direct or indirect, from an external energy source, supplying energy non-invasively, without any penetration through the patient's skin to power the rotating body of a turbine pump.

According to another aspect of the invention, the turbine pump according to the present invention can be adapted in a left ventricular assist device (LVAD).

According to a further aspect of the invention, the turbine pump system comprises a fixation of the heart pump apparatus to a structure of the human body comprising bone.

According to an additional aspect of the invention, the system comprises at least one switch implantable in the patient for manually and non-invasively controlling the device.

In another preferred embodiment, the system comprises a wireless remote control for non-invasively controlling the device.

In a preferred embodiment, the system comprises a hydraulic operation device for operating the apparatus.

In one embodiment, the system comprises a motor or a pump for operating the apparatus.

Additional preferred features, advantages and favorable embodiments of the invention, are evident from the dependent claims, and also in the following from description of the embodiments.

BRIEF DESCRIPTION OF DRAWINGS

The invention is now described {by way of example} with reference to the accompanying drawings, in which:

FIG. 1 schematically shows in a side view the principle of a turbine pump according to an embodiment of the present invention placed inside the aorta of a human patient.

FIG. 2a-b schematically shows, in perspective views and in cross-sectional views a stator and a rotating body of the turbine pump, according an embodiment of the present invention, the rotating body provided with blades of different design and configuration.

FIG. 15 shows a fixation system.
FIG. 16 shows a fixation system.

FIGS. 56-65 shows flow chars of operation methods.

DETAILED DESCRIPTION OF EMBODIMENTS

Figure 3:
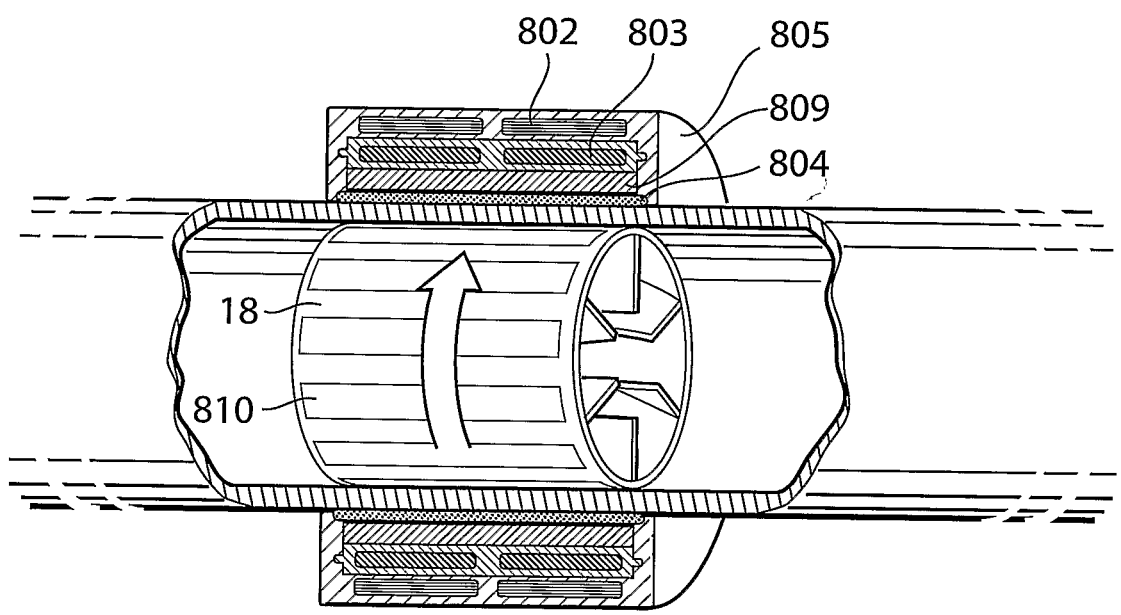
FIG. 3a-c schematically shows in a side view the principle of a turbine pump according to another embodiments of the present invention placed in a blood vessel in a human patient.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

As evident from FIGS. 1 and 3, it is shown a turbine pump 10 of a heart pump apparatus comprising a turbine wheel 12 and a suitable stator 14. FIG. 1 shows the turbine pump 10 placed in a blood stream 16, such as in the aorta, in a human patient. The turbine pump 10 of the present invention provides the heart 3 of the human patient with additional pumping capacity. The turbine pump 10 can also be adapted to be placed in the heart, in the pulmonary artery, or in the blood stream in the abdominal aorta of the human patient. Consequently, FIG. 3a shows the turbine pump 10 placed in a general blood stream 16, such as a blood vessel 17, in the human patient. 132. The heart pump apparatus according to claim 6 or 120, wherein the heart pump further comprises confining elements adapted to confine said rotating body in the longitudinal extension of the artery in which it is placed.

Further, FIG. 1 shows a confining portion 801 of the longitudinal extension of the artery. The confining portion 801 confines the rotating body in the artery in which it is placed. This eliminates the risk of the rotating body passing further into the heart. According to other embodiments the rotating body is confined in the artery by the magnetic coupling supplying the propulsion to the rotating body.

FIGS. 2a-b shows embodiments of the turbine pump 10. The turbine wheel 12 is preferably in the form of a longitudinal rotating body 18. The rotating body 18 has a cylindrical shape defined by an external cylindrical wall 20 with an outer surface 22 and an inner surface 24. Internally the rotating body 18, blades 26 are provided. The blades 26 are extending radially or non-radially from the inner surface 24. The rotating body 18 have a longitudinal centre C in line with the blood stream 16. The respective blades 26 are not extending from the inner surface 24 all away to the centre C of the rotating body 18. In that respect, the respective blades 26 have a first end 28 attached to the rotating body 18 and a second outer free end 30, which second free end 30 is placed at a distance from the centre C of the rotating body 18. Hence, the centre C of the rotation body 18 is preferably a void space extending in the longitudinal direction L of the rotating body 18. Consequently, the turbine pump 10 according to the present invention is a centre axis free turbine pump.

The internal blades 26 arranged on the inner surface 24 of the rotating body 18 could have the purpose of eliminating friction generated by the blood that flows through the inside of the rotation body 18. The blades 26 can also make the external wall 20 of the rotating body 18 more stiffened.

As evident from FIGS. 2a-b, the rotating body 18 can be provided with blades 26 of different design and configuration. The incidence angles and the attack angles of the blades 26 are variable so that they can be arranged to yield the highest possible efficiency.

The turbine pump 10 comprises a device for rotation of the rotating body 18. The device for rotation of the rotating body 18 can be a part of an electrically controlled arrangement.

As a device for rotation of the rotating body, the stator 14 of the turbine pump is preferably provided. The stator 14 is preferably adapted to be placed outside the blood vessel 17 and opposite the rotating body 18. The electrically controlled arrangement includes elements E, shown with phantom lines in FIGS. 2a-b, for receiving current to increase or decrease a magnetic field created at the stator 14, for providing rotation of the rotating body 18, by creating a magnetic field between the poles of the stator 14, that is provided for increasing or decreasing the rotation of the rotating body 18. Consequently, a turbine pump system for assisting the heart of a patient is provided, comprising a rotating body 18 and a stator 14.

According to an embodiment, as evident from FIG. 3b, at least two rotating bodies 18', 18" can be implanted in sequence in the same blood vessel. If there are two rotating bodies in sequence, one 18' can be adapted to rotate clockwise (see arrow R1) and the following other rotating body 18" can be adapted to rotate counter clockwise (see arrow R2), or vice versa.

FIG. 3c shows an embodiment of the heart pump device showing the drive unit, in which the stator 802 and rotor 18 is placed on the outside of the artery. The stator 802 and rotor 803 is confined in a housing 805 and is separated from the artery by a protective sheet 804 placed between the rotor 803 and artery, the protective sheet is preferably a thin plastic sheet providing a smooth surface for the rotor 803 to slide against. The rotor 803 rotates magnetic elements 809 which in turn rotates magnetic elements 810 of the rotating body 18 placed inside of the artery, by the magnetic elements 809 of the rotor 803 being in magnetic connection with the magnetic elements 810 of the rotor 18. In some embodiments the magnetic elements 809 of the rotor, is the rotor 803.

The present invention also relates to a method of surgically placing a rotating body 18 of a turbine pump 10 in a patient via a laparoscopic thoracic approach, the method comprising the steps of: inserting a needle or a tube like instrument into the thorax of the patient's body; using the needle or a tube like instrument to fill the thorax with gas thereby expanding the thoracic cavity; placing at least two laparoscopic trocars in the patient's body; inserting a camera through one of the laparoscopic trocars into the thorax; inserting at least one dissecting tool through one of said at least two laparoscopic trocars and dissecting an intended placement area of the patient; placing the rotating body 18 in any part of the blood stream in the thorax; and connecting a source of energy for powering the device.

The present invention also relates to an operation method for surgically placing a rotating body 18 of a turbine pump 10 in a patient, the method comprising the steps of: cutting the patient's skin; opening the thoracic cavity; dissecting a placement area where to place the rotating body 18 inside a blood stream in the heart 3, or the aorta 4 or inside the pulmonary artery of the human patient; placing the a rotating body 18 in the placement area; and connecting a source of energy for powering the device.

The present invention also relates to a method of surgically placing a rotating body 18 of a turbine pump 10 in a patient via a laparoscopic abdominal approach, the method comprising the steps of: inserting a needle or a tube like instrument into the abdomen of the patient's body; using the needle or a tube like instrument to fill the abdomen with gas thereby expanding the abdominal cavity; placing at least two laparoscopic trocars in the patient's body; inserting a camera through one of the laparoscopic trocars into the abdomen; inserting at least one dissecting tool through one of said at least two laparoscopic trocars and dissecting an intended placement area of the patient; placing the rotating body 18 in the blood stream in the abdominal aorta; and connecting a source of energy for powering the device.

The present invention also relates to an operation method for surgically placing a rotating body 18 of a turbine pump 10 in a patient, the method comprising the steps of: cutting the patient's skin; opening the abdominal cavity; dissecting a placement area where to place the rotating body 18 in region of the abdominal aorta; placing the a rotating body in the blood stream in the abdominal aorta; and connecting a source of energy for powering the device.

The present invention also relates to an operation method for surgically placing a rotating body 18 of a turbine pump 10 and stator 14 of a turbine pump 10 in a patient, via a laparoscopic thoracic approach, the method comprising the steps of: inserting a needle or a tube like instrument into the thorax of the patient's body; using the needle or a tube like instrument to fill the thorax with gas thereby expanding the thoracic cavity; placing at least two laparoscopic trocars in the patient's body; inserting a camera through one of the laparoscopic trocars into the thorax; inserting at least one dissecting tool through one of said at least two laparoscopic trocars and dissecting an intended placement area in the vascular system of the patient; placing the rotating body 18 in any part of the blood stream in the thorax, inside a blood stream of the blood vessel in the heart 3, or the aorta 4 or inside the pulmonary artery of the patient; placing the a stator 14 in the placement area, outside the blood stream of the blood vessel, outside the heart 3, or the aorta 4 or outside the pulmonary artery of the patient, placing said stator 14 on the outside of said rotating body 18, supplying wireless energy to said rotating body 18 causing rotating movement of said rotating body 18; and connecting a source of energy for powering said stator.

The present invention also relates to an operation method for surgically placing a rotating body 18 of a turbine pump 10 and stator 14 of a turbine pump 10 in a patient, the method comprising the steps of: cutting the patient's skin; opening the thoracic cavity; placing the rotating body 18 in any part of the blood stream in the thorax, inside a blood stream of the blood vessel in the heart 3, or the aorta 4 or inside the pulmonary artery of the patient; placing the a stator 14 in the placement area, outside the blood stream 16 of the blood vessel 17, outside the heart 3, or the aorta 4 or outside the pulmonary artery of the patient, placing said stator 14 on the outside of said rotating body 18, supplying wireless energy to said rotating body 18 causing rotating movement of said rotating body 18; and connecting a source of energy for powering said stator.

The present invention also relates to an operation method for surgically placing a rotating body 18 of a turbine pump and stator 14 of a turbine pump 10 in a patient, via a laparoscopic abdominal approach, the method comprising the steps of: inserting a needle or a tube like instrument into the abdomen of the patient's body; using the needle or a tube like instrument to fill the thorax with gas thereby expanding the abdominal cavity; placing at least two laparoscopic trocars in the patient's body; inserting a camera through one of the laparoscopic trocars into the abdomen; inserting at least one dissecting tool through one of said at least two laparoscopic trocars and dissecting an intended placement area in the region of the abdominal aorta of the patient; placing the rotating body 18 inside the blood stream 16 in the abdominal aorta of the patient, placing the a stator 14 in the placement area, outside the blood stream of the abdominal aorta, placing said stator 14 on the outside of said rotating body, supplying wireless energy to said rotating body 18 causing rotating movement of said rotating body 18; and connecting a source of energy for powering said stator.

The present invention also relates to an operation method for surgically placing a rotating body 18 of a turbine pump 10 and stator 14 of a turbine pump 10 in a patient, the method comprising the steps of: cutting the patient's skin, opening the abdominal cavity; placing the rotating body inside the blood stream 16 in the abdominal aorta of the patient, placing the a stator 14 in the placement area, outside the blood stream of the abdominal aorta, placing said stator 14 on the outside of said rotating body 18, supplying wireless energy to said rotating body 18 causing rotating movement of said rotating body 18; and connecting a source of energy for powering said stator.

The present invention also relates to a method according to any of the operation methods or methods of surgically placing a rotating body 18 and/or a stator 14 as mentioned above, wherein said energy source is using energy, direct or indirect, from an external energy source, supplying energy non-invasively, without any penetration through the patient's skin to power the rotating body of a turbine pump 10.

According to another aspect, the turbine pump 10 according to the present invention can be adapted in a left ventricular assist device (LVAD). The LVAD is a surgically implanted, mechanical pump-type device, which helps maintain the pumping ability of a damaged heart. According to the state of the art, a tube pulls blood from the left ventricle into a pump (VAD), see FIG. 4. The pump then sends blood into the aorta. This effectively helps the weakened ventricle. There exists various kinds of pumps (VAD) on the market. For instance, there is one pump that contains a metal plate that pushes on a plastic blood sac, forcing the blood out of the sac. The metal plate is driven by a miniature electric motor. According to the present invention, the rotating body of the turbine pump can be arranged in a tube that pulls blood from the aorta, and sends back blood into the aorta.

FIG. 3c The heart pump according to claim 119, wherein said second part is adapted to be a rotor, being cylindrical and placed outside said blood vessel, when implanted, adapted to be in magnetic connection with said rotating body such that said rotating body follows the rotations of said second part.

Figure 4A:
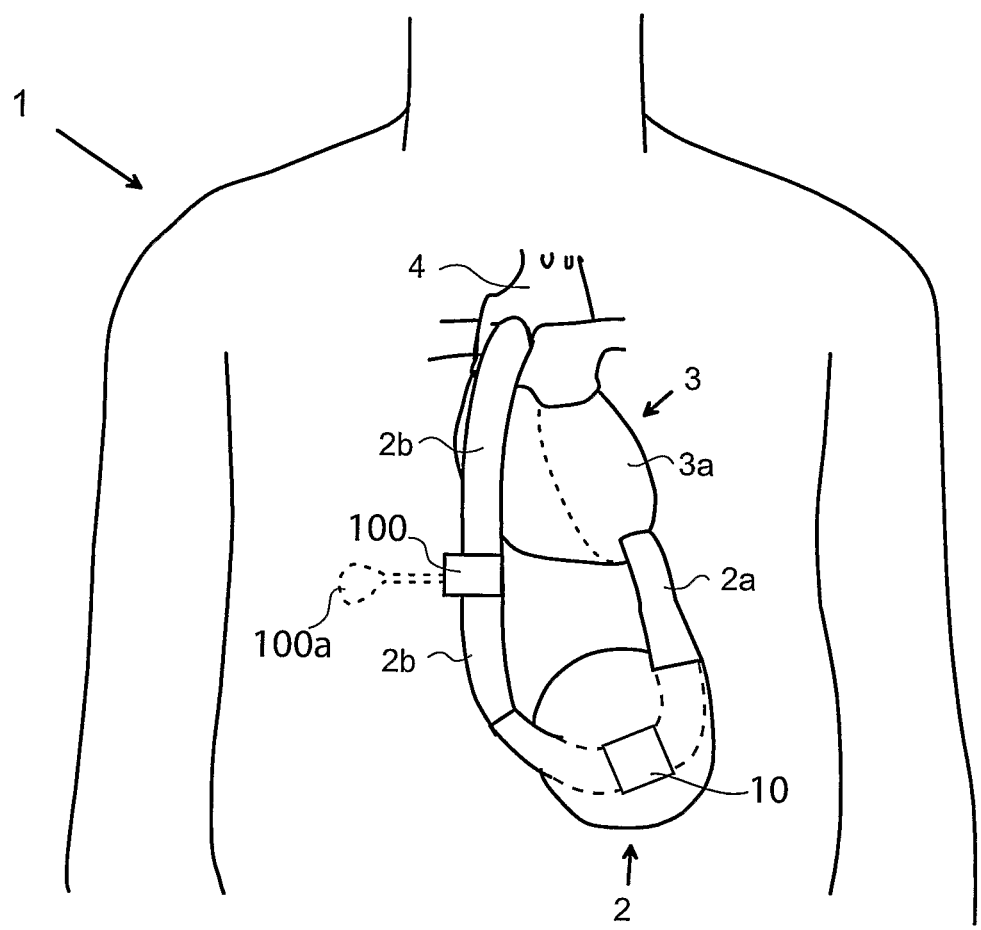
FIG. 4a is an overview of the body of a patient having an implanted heart pump according to the invention.
Figure 4:
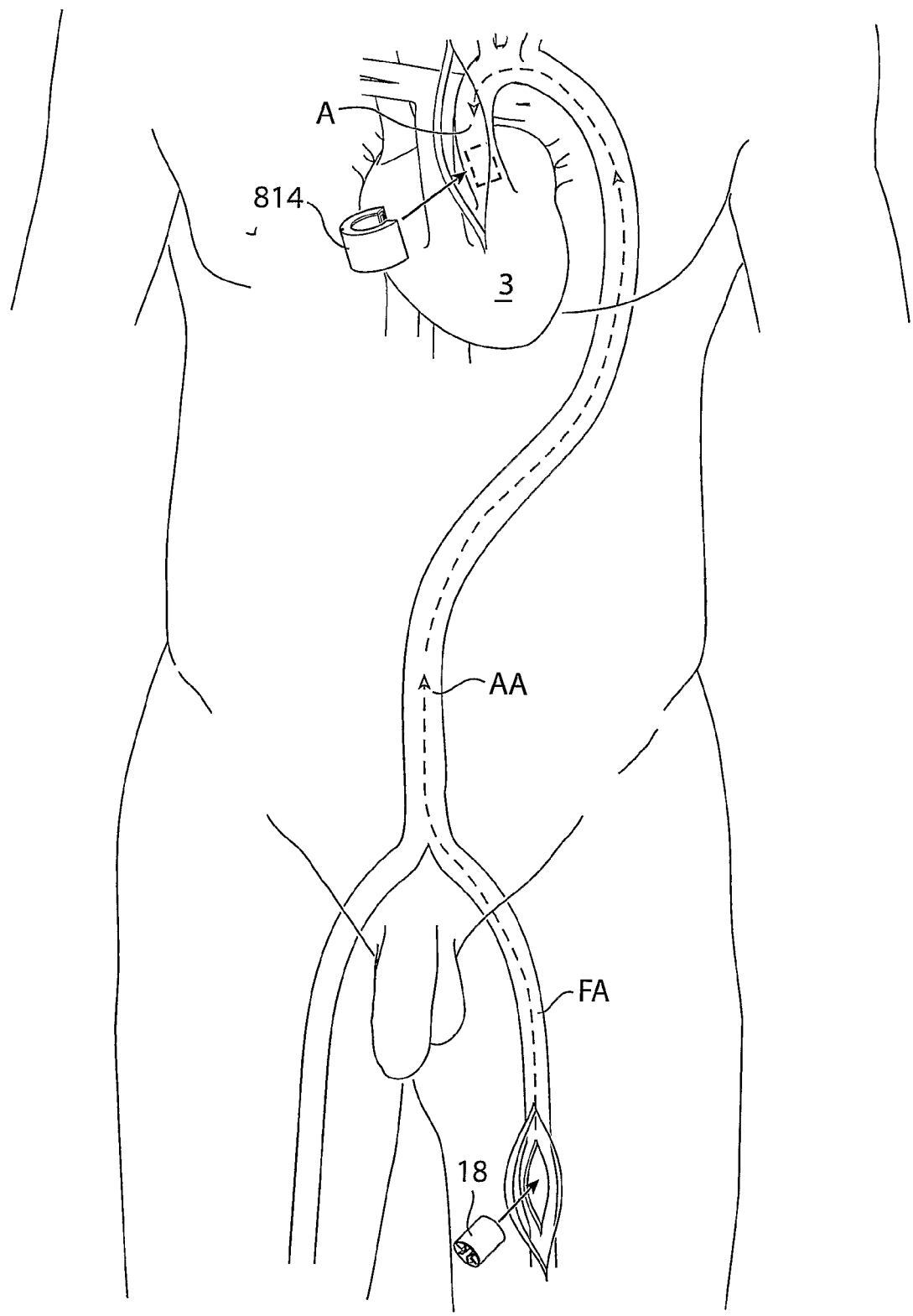
FIGS. 4b-4e shows different steps of operation methods for placing the device according to the invention.

FIG. 4 shows a patient 1 having an implanted heart pump 2, here illustrated a pump (VAD) of a left ventricular assist device (LVAD). As mentioned above, according to one aspect of the present invention, the implanted heart pump 2 can be the turbine pump 10, as shown with phantom lines in FIG. 4, according to one embodiment of the present invention. The implanted heart pump 2 is connected to the left ventricle 3a of the patient's heart 3 by means of a first tube 2a. The heart pump 2 is also connected to the aorta, generally designated 4, of the patient 1 by means of a second tube 2b. In this way, during operation the heart pump supplements or replaces the blood pumping operation of the patient's heart 3.

FIG. 4b shows an operation method for surgically placing a rotating body 18 of a turbine pump 10 in an artery of a patient, via a laparoscopic inguinal approach, the method comprising the steps of: inserting a tube like instrument into the femoral artery FA of the patient's body and using the instrument to guide said rotating body 18 through the femoral artery FA to the aorta A and releasing the rotating body 18 inside of the aorta A. Thereafter the method comprises the step of placing a drive unit 814, at least partially encircling the aorta A. The drive unit 814 can be placed in a thoracic approach, by opening the thorax of the patient, or in an abdominal approach, reaching the heart 3 of the patient through the thoracic diaphragm.

Figure 4C:
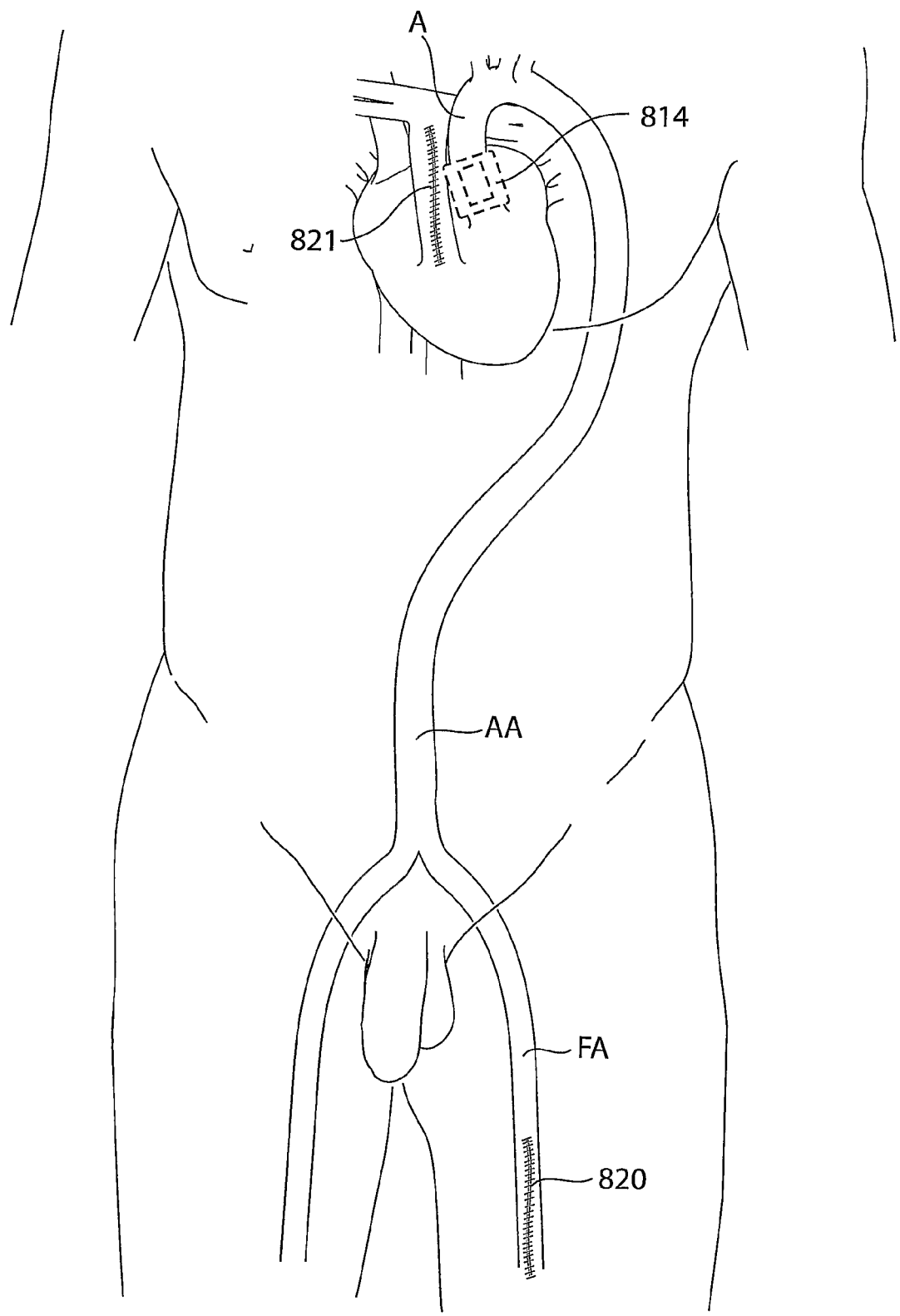
Figure 4:
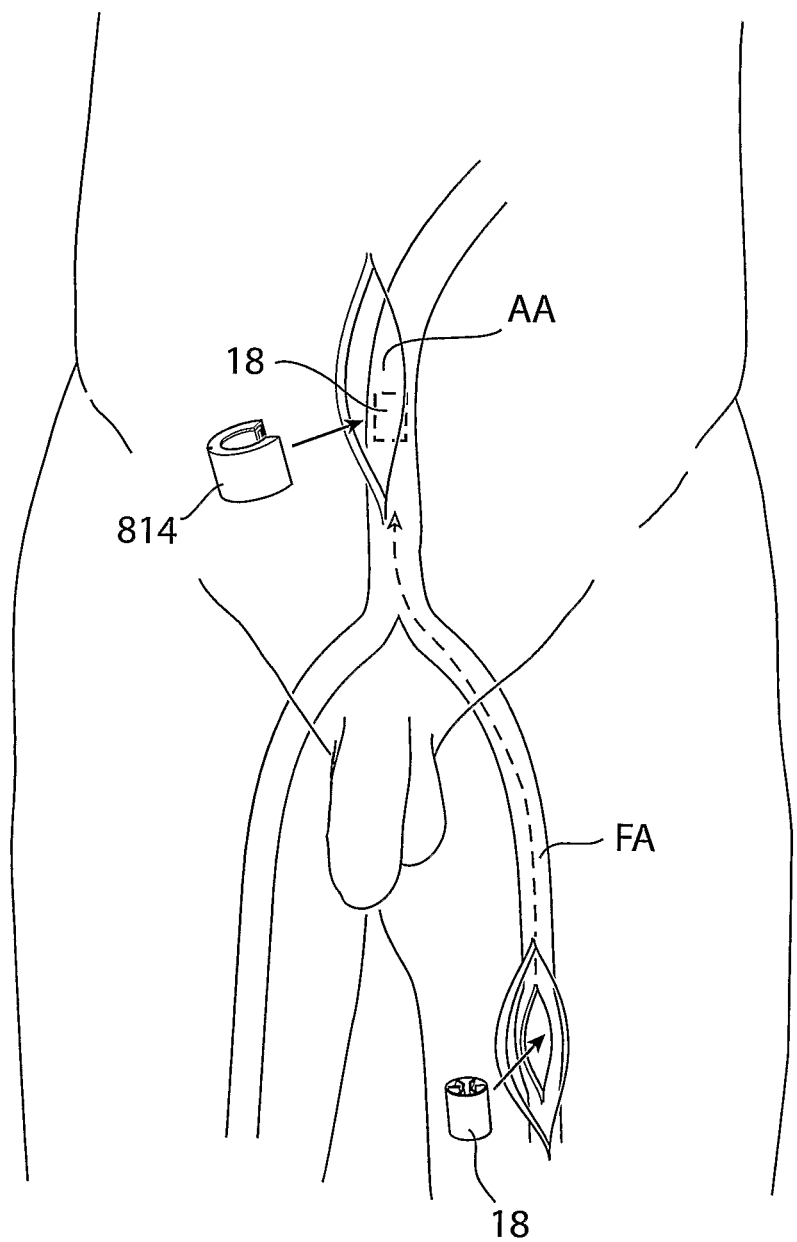
Figure 4:
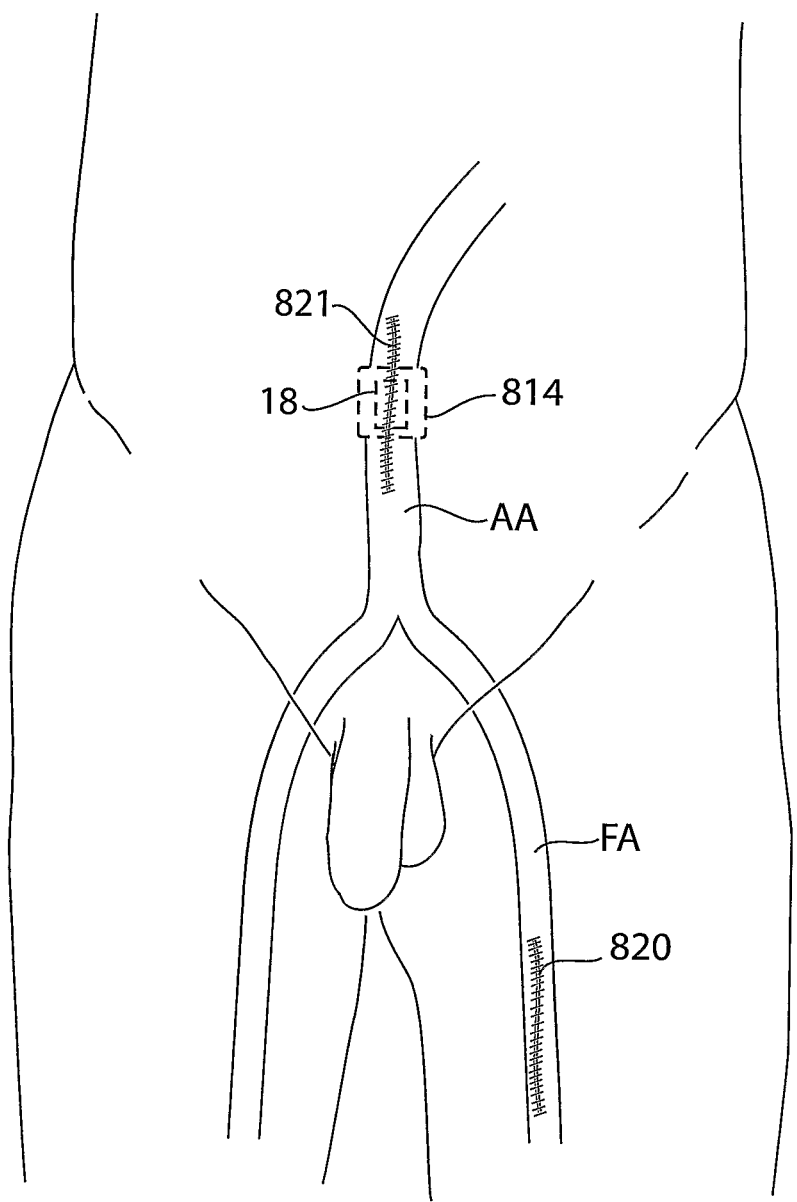

FIG. 4c shows a frontal view of the human patient after the operation has been performed and the incisions in the inguinal region 820 and the thorax 821 has been closed using sutures or staples. The drive unit 814 (here shown in phantom lines) is placed at least partially encircling the aorta A in proximity to the heart 3.

FIG. 4d shows an operation method for surgically placing a rotating body 18 of a turbine pump 10, via a laparoscopic inguinal approach. The method comprises the steps of: inserting a tube like instrument into the femoral artery FA of the patient's body, using the instrument to guide the rotating body 18 through the femoral artery FA to the abdominal aorta AA. After the rotating body 18 has been guided to the abdominal artery AA through the femoral artery FA the rotating body 18 is released inside the artery. The drive unit 814 is inserted through an incision in the abdomen and placed at least partially encircling the abdominal artery AA, such that the drive unit 814 is placed in magnetic contact with the rotating body 18.

FIG. 4e shows a frontal view of the patient after the incisions in the inguinal area 820 and the incisions in the thorax 821 has been closed using sutures or staples. The drive unit 814 (here shown in phantom lines) are placed partially encircling the abdominal artery AA in the abdomen.

A blood clot removal device 100 according to the invention is shown provided in the second tube 2b of the heart pump 2, i.e., in the tube leading to the aorta 4 of the patient 1. This means that part of the blood flow passageway provided by the second tube 2b is replaced by a blood flow passageway in the blood clot removal device 100. The blood clot removal device 100 is thus an artificial device insertable in an artificial blood vessel of the patient. The function of the clot removal device is to remove any blood clots in the blood transported by the second tube 2b. These blood clots are preferably moved to a place free inside the body of the patient. However, they could alternatively be collected in a collecting volume, such as a bag 100a connected to the blood clot removal device 100 for subsequent removal or storage. A preferred storage capacity of the bag 100a can be more than 100 milliliters, for example. The blood clot removal device is an artificial device but could be inserted directly into a blood vessel of the patient or connected between two ends of a blood vessel.

The clot removal device is preferably insertable in a blood flow passageway of the patient via surgery and is placed in the patient's abdomen or thorax or cephalic or neck region or retroperitoneal or any limb of the patient.

Figure 5:
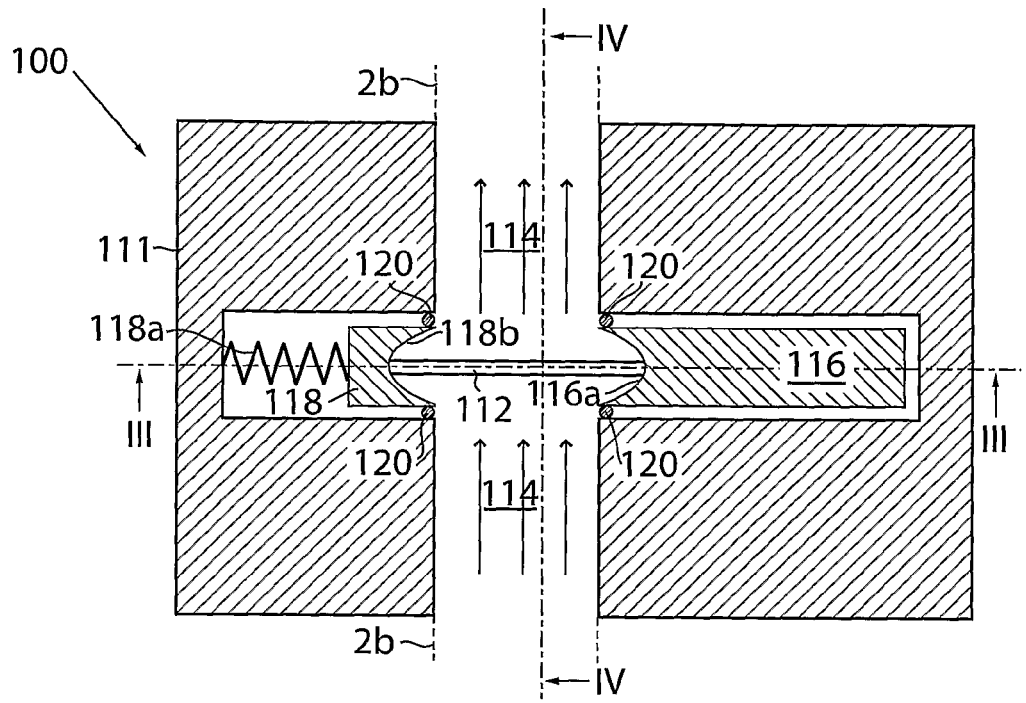
FIG. 5 is a sectional view of a clot removal device according to the invention.
Figure 6:
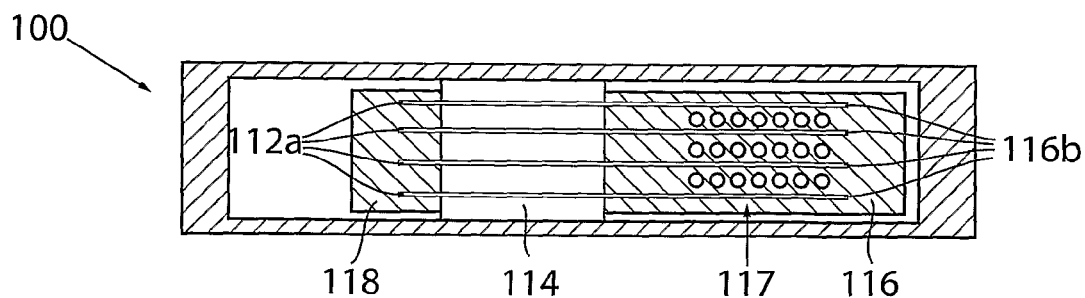
FIG. 6 is a cross sectional view of the clot removal device of FIG. 5 taken along the line before a cleaning operation.

The design of a first preferred embodiment of the blood clot removal device 100 will now be described in detail, with reference to FIGS. 5-7. FIG. 5 shows a sectional view wherein the blood clot removal device 100 is provided in the blood flow passageway provided by the second tube 2b. A filter 112 is provided across the blood flow passageway 114 formed in a housing 111 with the function of stopping potential blood clots brought forward in the second tube 2b by the blood flow, indicated by arrows in the figure. In this preferred embodiment, the filter 112 comprises a plurality of preferably equally spaced strips 112a of some suitable material, such as biocompatible metal or plastic. These strips 112a are preferably arranged mutual parallel.

The distance between two adjacent strips is small enough to stop any blood clots. Thus, the distance is preferably less than 2 millimeters, and even more preferably less than 1.0 millimeters, but if the goal is to protect the brain from larger clots only the distance could be larger. Although the blood flow passageway 114 in the preferred embodiment has an essentially square cross-sectional shape, it will be realized that it can take any suitable shape, such as rectangular or circular.

By providing a plurality of strips 112a as a filter across the blood flow passageway 114, a laminar blood flow is achieved downstream of the filter, which is advantageous in a blood clot preventing perspective. The blood flow configuration can be further enhanced by giving the plurality of strips 112a a desired cross-sectional shape, although the rectangular shape shown in FIG. 7 will be adequate for most purposes.

A first piston 116 is provided movable in a direction essentially perpendicular to the direction of the blood flow passageway 114, i.e., essentially perpendicular to the direction of the blood flow. This first piston 116 is driven by some suitable actuator means, such as pressurized air, a solenoid arrangement, an electrical servo motor or the like. A motor could be used to build up a stored power that could be released very fast, one example being a spring. In the preferred embodiment, pressurized air acts as the actuator means, since by latching the piston by means of a suitable latching means for the piston, building up the air pressure, and subsequently releasing the piston, very high speed of the piston is achieved, with enables short cleaning times of the filter.

The outer end portion of the first piston 116, i.e., the end portion facing the blood flow passageway 114, is essentially flush with the wall of the blood flow passageway in a non-active state of the blood clot removal device 100. Also, the outer end portion is provided with a concave portion or recess 116a (exaggerated in the figures) in order to act as a blood clot capturing means, as will be explained below.

The strike range of the first piston 116 is such that it extends all way across the blood flow passageway 14, as will be explained below with reference to FIGS. 8-11. A number of channels 116b corresponding to the number of strips 112a is provided in the first piston 16 to accommodate the strips when the first piston is in an extended position.

The first piston 116 is also provided with a plurality of through holes 117 in the direction of the blood flow passageway. These through holes will allow blood to flow through the blood flow passageway also during a cleaning operation, as will be explained below with reference to FIG. 12.

A second piston 118 is provided across the blood flow passageway 114 from the first piston 116. Also this second piston 118 is movable in a direction essentially perpendicular to the direction of the blood flow passageway 114 and is biased in the direction thereof by means of a spring 118a, for example. Likewise, the outer end portion of the second piston is provided with a recess 18b similar to the recess 116a of the first piston 116.

The first and second pistons 116, 118, are sealed to the housing 111 by means of a respective sealing 120, such as an O sealing.

Figure 8:
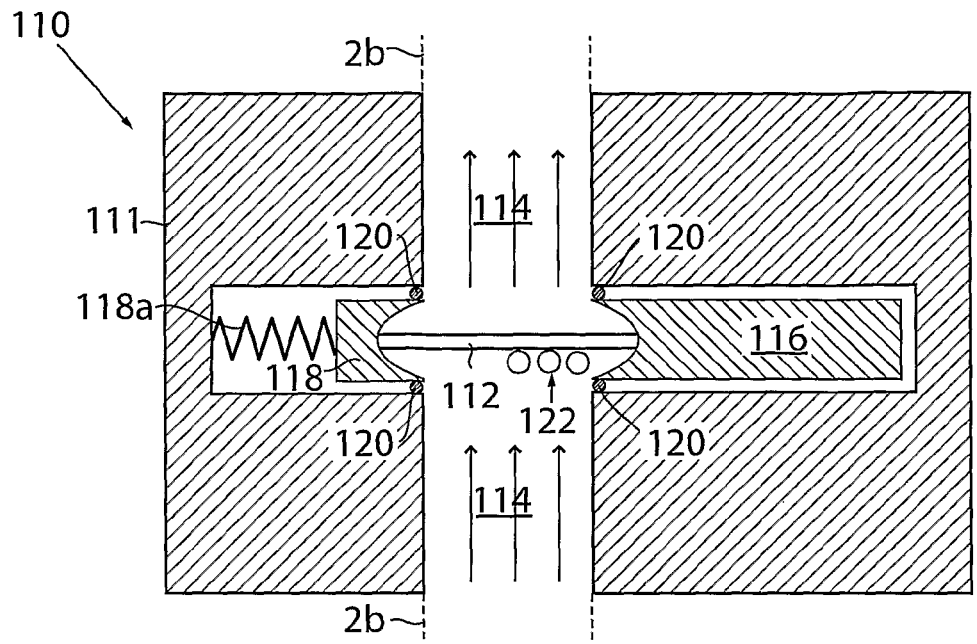
FIG. 8 is a sectional view similar to that of FIG. 5 showing blood clots before a clot removal operation.

A preferred embodiment of the method according to the invention will now be described with reference to FIGS. 8-11, showing different operational steps of the above-described device. FIG. 8 is a view similar to that of FIG. 5. However, this figures shows the blood clot removal device 100 during operation, wherein blood clots, generally designated 122, have assembled on the filter 112.

Figure 9:
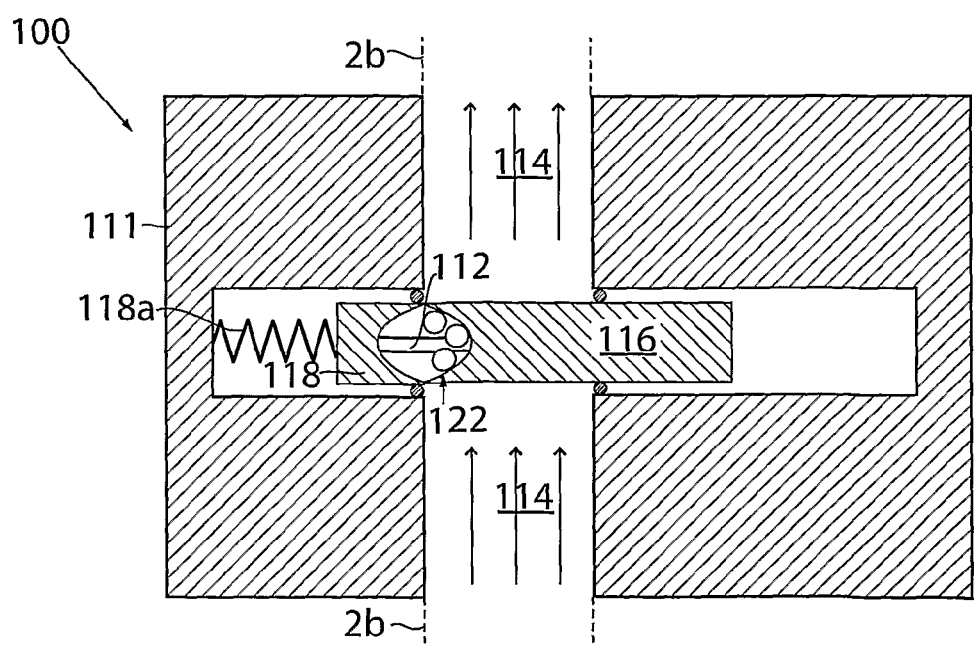
FIG. 9 is a sectional view similar to that of FIG. 5 during a first step of a clot removal operation.

In FIG. 9, the first piston 116 has moved linearly from the retracted starting position shown FIG. 8 to an extended position, wherein the outer end portion thereof is in contact with the second piston 118. Due to the recess 116a in the outer end of the first piston 116, the blood clots 122 have been assembled in the recess 116a, whereby they have been brought with the first piston 116 during the movement thereof. In the step shown in FIG. 9, the blood clots are confined in the recess 116a between the first and second pistons 116, 118.

Figure 10:
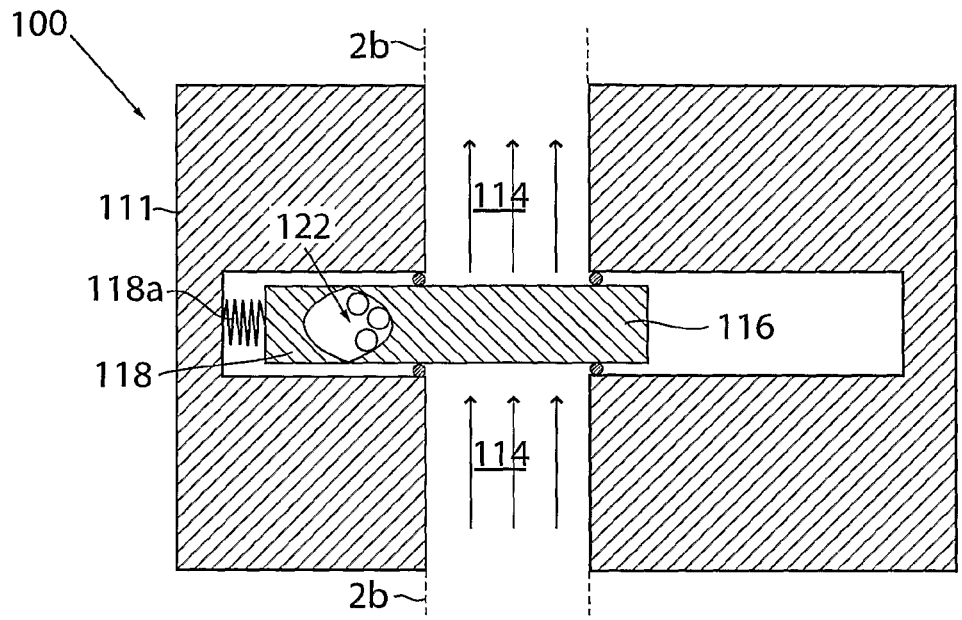
FIG. 10 is a sectional view similar to that of FIG. 5 during a second step of a clot removal operation.

By moving the first piston 116 an additional distance from the position shown in FIG. 9, the second piston 118 is pushed against the force of the spring 118a to a fully retracted position, see FIG. 10. The plurality of strips 112a is in this position fully received in a respective channel 116b in the first piston. It is seen that the outer ends of the first and second pistons define an unobstructed cavity in which the blood clots are confined. It is thereby possible to remove these by some suitable means. One such means could be a third piston 124, which is movable in a direction perpendicular to both the direction of the blood flow passageway 114 and the direction of movement of the first and second pistons 116, 118. This third piston, the movement of which could be controlled by means of pressurized air, a solenoid, an electric motor etc., scrapes off the blood clots collected by the first piston 116 and moves them to a place outside of the blood clot removal device 100 and the blood flow passageway 114.

Figure 11:
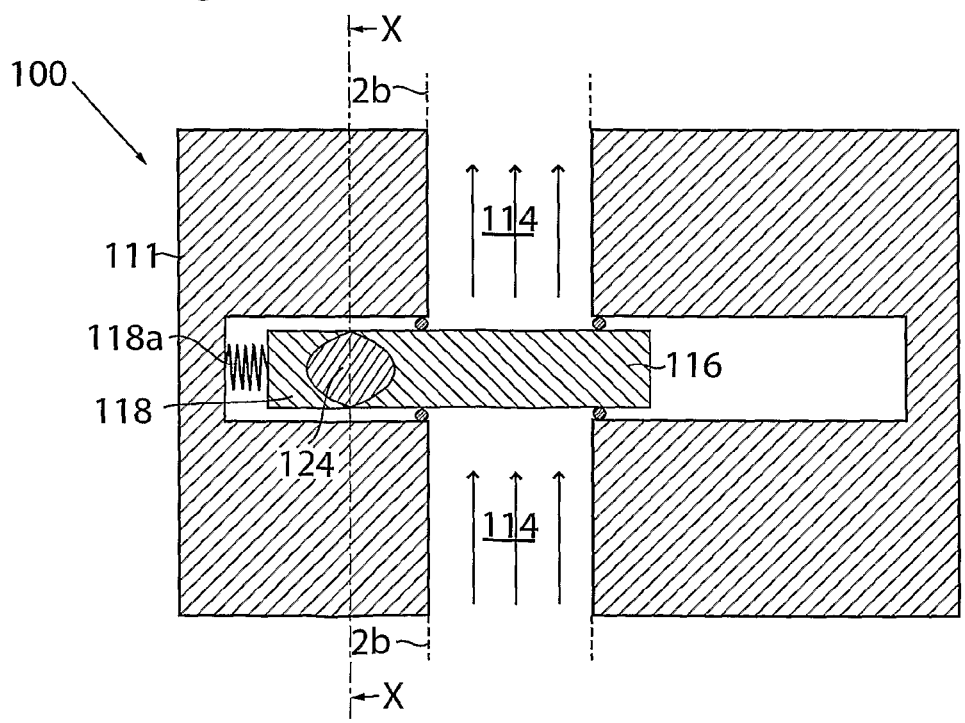
FIG. 11 is a sectional view similar to that of FIG. 5 during a third step of a clot removal operation.
Figure 12:
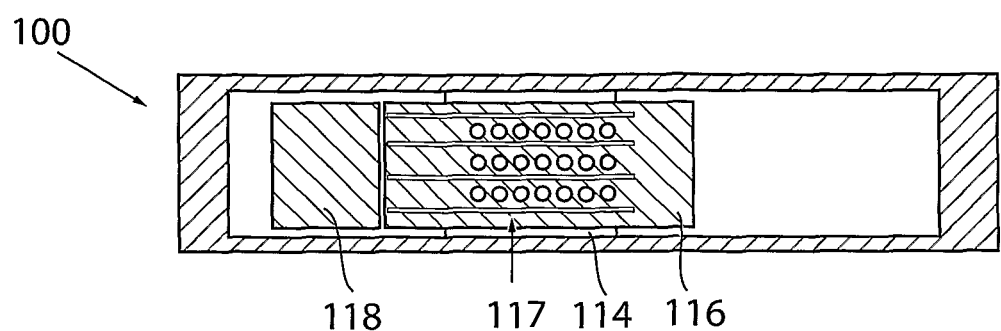
FIG. 12 is a cross sectional view similar to that of FIG. 6 but during a cleaning operation.

FIG. 12 shows a side view of the first piston 116 in a fully extended position, i.e., corresponding to the view of FIG. 11. It is here seen that in this position the through holes 117 will be aligned with the blood flow passageway 114, thereby allowing blood to flow therethrough also during cleaning of the filter 112.

Figure 13:
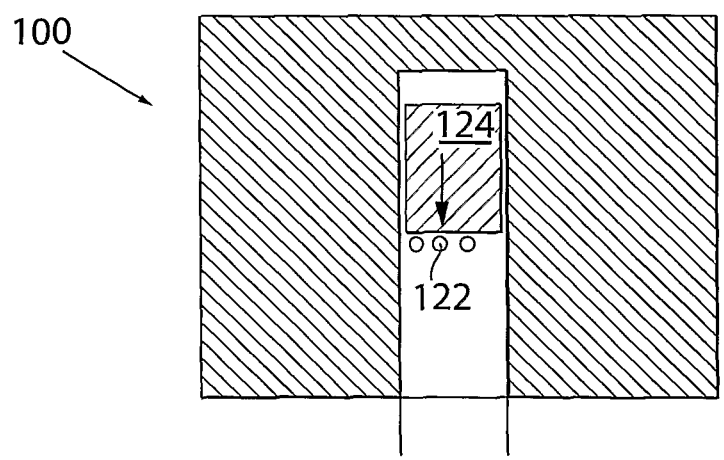
FIG. 13 is a sectional view of the clot removal device of FIG. 11 taken along the line X-X showing a clot ejection piston before ejection of clots.
Figure 14:
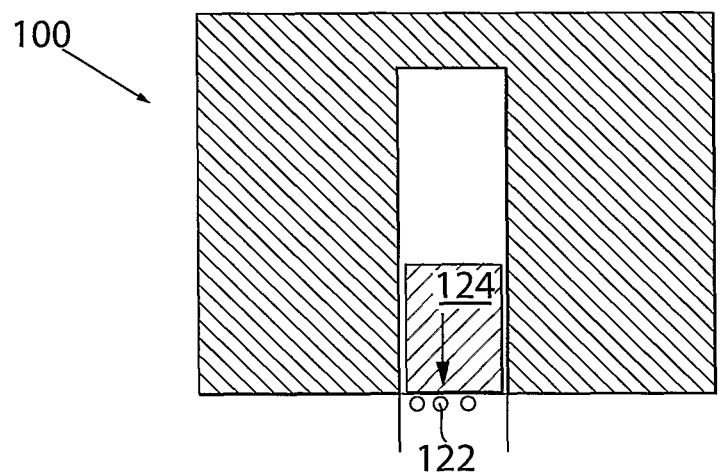
FIG. 14 is a view similar to that of FIG. 12 but after ejection of clots.

FIG. 13 shows a cross-sectional view taken along line X-X of FIG. 11. It is here seen that the third piston 124 collects the blood clots 122 during a downward movement, indicated by an arrow in the figure. The clots are ejected from the blood clot removal device 100 when the third piston 124 has reached its lower end position, shown in FIG. 14.

Again with reference to FIG. 10, it will be realized that pressurized air can be used for ejecting the collected blood clots from the cavity formed by the first piston 116 and the second piston 118.

FIG. 15-28 shows the fixation of a heart pump apparatus to a structure of the human body comprising bone 240. The structure could be the sternum, a part of the rib cage, comprising one or more ribs or a part of the vertebral column comprising at least one vertebra. According to one embodiment the heart pump apparatus 10 is fixated to the structure of the human body comprising bone 240 trough a fixating member 241 said fixating member could comprise a plate 242 which is in contact with the structure of the human body comprising bone 240. The heart pump apparatus 10 could also be fixated to the structure of the human body comprising bone 240 using a second fixating member 241b which also could comprise a plate 242b in which in turn could be in contact with the structure of the human body comprising bone 240.

FIG. 15 shows an embodiment where a heart pump apparatus 10 is fixated to a structure of the human body comprising bone 240. The structure could be the sternum, a part of the rib cage comprising one or more ribs or a part of the vertebral column structure comprising at least one vertebra. According to the embodiment the heart pump apparatus 10 comprises a first fixating member 241a comprising a plate 242a and a second fixating member 241b comprising a plate 242b. The first and second fixating members are attached to each other using through-going screws 243 placed from the anterior side A of the structure of the human body comprising bone 240. An alternative embodiment could comprise screws placed from the posterior side P of the structure of the human body comprising bone 240. The first fixating member 241a and the second fixating member 241b clamp the structure of the human body comprising bone 240. The fixating member 241a could be in contact with a connecting arm 244 which in turn could be in contact with a heart pump device.

FIG. 16 shows an embodiment where the heart pump apparatus 10 is fixated to a structure of the human body comprising bone 240 using only one fixating member 241a comprising a plate 242a. The structure could be the sternum, a part of the rib cage comprising one or more ribs or a part of the vertebral column structure comprising at least one vertebra. Through-going screws 243 is placed form the anterior side A the structure of the human body comprising bone 240 and fixated in the plate 242a. An alternative embodiment could comprise screws placed from the posterior side P of the structure of the human body comprising bone 240 in which case the screws could be fixated in nuts placed in connection with the structure of the human body comprising bone, or fixated in directly in the bone of the structure of the human body comprising bone 240. The fixating member 241a could be in contact with a connecting arm 244 which in turn could be in contact with a heart pump device.

Figure 17:
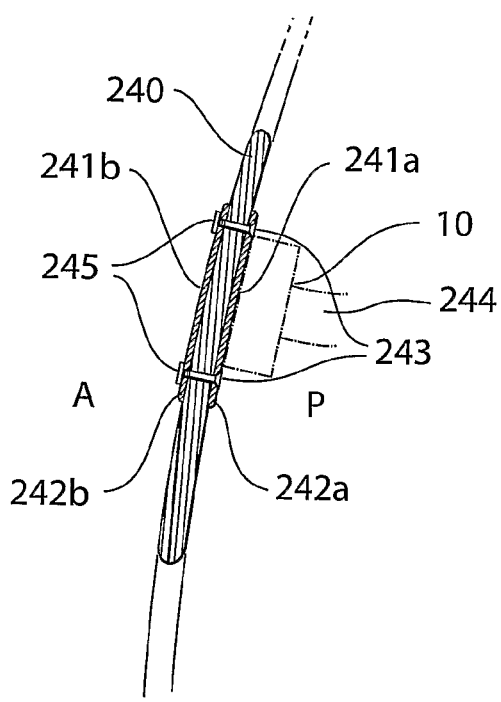
FIG. 17 shows a fixation system.

FIG. 17 shows an embodiment where the heart pump apparatus 10 is fixated to a structure of the human body comprising bone 240. The structure could be the sternum, a part of the rib cage comprising one or more ribs or a part of the vertebral column comprising at least one vertebra. According to the embodiment the heart pump apparatus 10 comprises a first fixating member 241a comprising a plate 242a and a second fixating member 241b comprising a plate 242b. The first and second fixating members are attached to each other using through-going screws 243 placed from the posterior side P of the structure of the human body comprising bone 240. The screws are fixated to nuts 245 placed on the anterior side of the structure comprising bone 240. An alternative embodiment could comprise screws placed from the anterior side A of the structure of the human body comprising bone 240, in which case the nuts is placed on the posterior side P of the structure comprising bone 240. The first fixating member 241a and the second fixating member 241b clamp the structure of the human body comprising bone 240. The fixating member 241a could be in contact with a connecting arm 244 which in turn could be in contact with a heart pump device.

Figure 18:
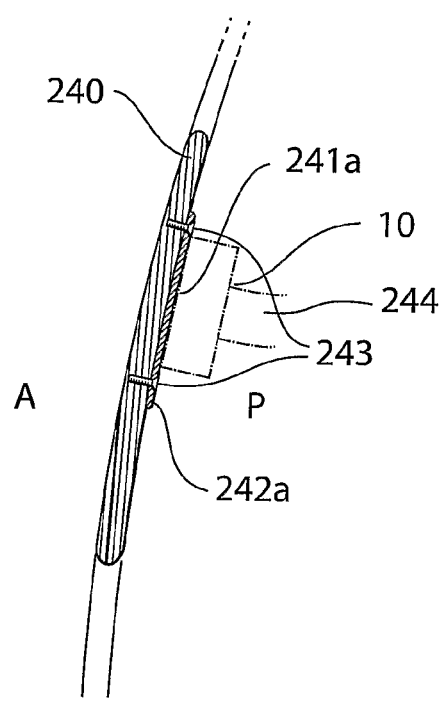
FIG. 18 shows a fixation system.

FIG. 18 shows an embodiment where the heart pump apparatus 10 is fixated to a structure of the human body comprising bone 240 using only one fixating member 241a comprising a plate 242a. The structure could be the sternum, a part of the rib cage comprising one or more ribs or a part of the vertebral column structure comprising at least one vertebra. Screws 243 that fixates the fixating member to the structure of the human body comprising bone is placed form the posterior side P the structure of the human body comprising bone 240. The screws fixates the fixating member to both the posterior and the anterior cortex of the structure of the human body comprising bone 240, however it is conceivable that the screws are fixated only to the anterior or posterior cortex. An alternative embodiment could comprise screws placed from the anterior side A of the structure of the human body comprising bone 240, in which case the fixating member 241a is placed on the anterior side A of the structure of the human body comprising bone 240.

Figure 19:
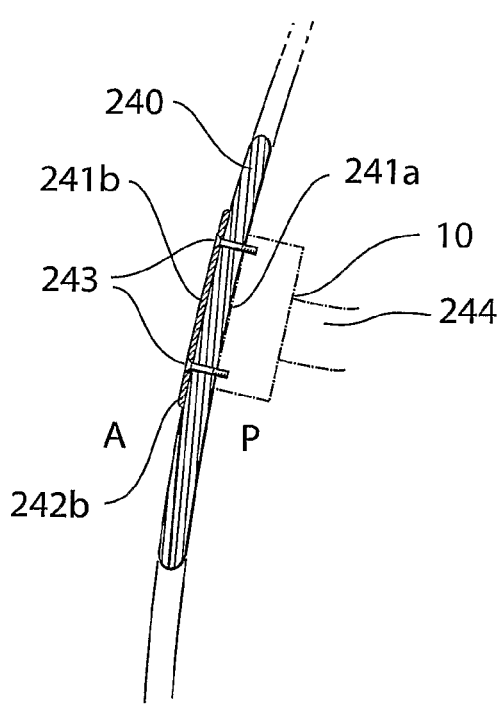
FIG. 19 shows a fixation system.

FIG. 19 shows an embodiment where the heart pump apparatus 10 is fixated to a structure of the human body comprising bone 240 using one fixating member 241b comprising a plate 242b, and one fixating member 241a without a plate. The structure could be the sternum, a part of the rib cage comprising one or more ribs or a part of the vertebral column structure comprising at least one vertebra. Screws 243 that fixates the fixating members 241a,b to the structure of the human body comprising bone 240 is placed form the anterior side A of the structure of the human body comprising bone 240 and fixated in the fixating member 241a. The first fixating member 241a and the second fixating member 241b clamp the structure of the human body comprising bone 240. The fixating member 241a could be in contact with a connecting arm 244 which in turn could be in contact with a heart pump device.

Figure 20:
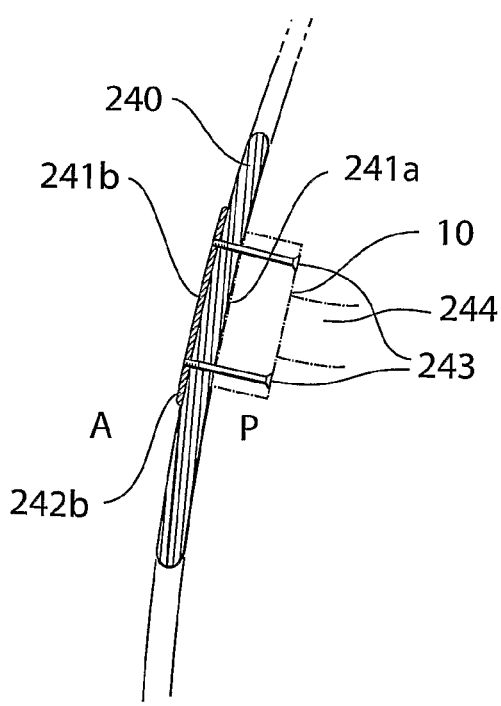
FIG. 20 shows a fixation system.

FIG. 20 shows an embodiment where the heart pump apparatus 10 is fixated to a structure of the human body comprising bone 240 using one fixating member 241b comprising a plate 242b, and one fixating member 241a without a plate. The structure could be the sternum, a part of the rib cage comprising one or more ribs or a part of the vertebral column structure comprising at least one vertebra. Screws 243 that fixates the fixating members 241a,b to the structure of the human body comprising bone 240 is placed form the posterior side P of the structure of the human body comprising bone 240 and fixated in the plate 242b of the fixating member 241b. The first fixating member 241a and the second fixating member 241b clamp the structure of the human body comprising bone 240. The fixating member 241a could be in contact with a connecting arm 244 which in turn could be in contact with a heart pump device.

Figure 21:
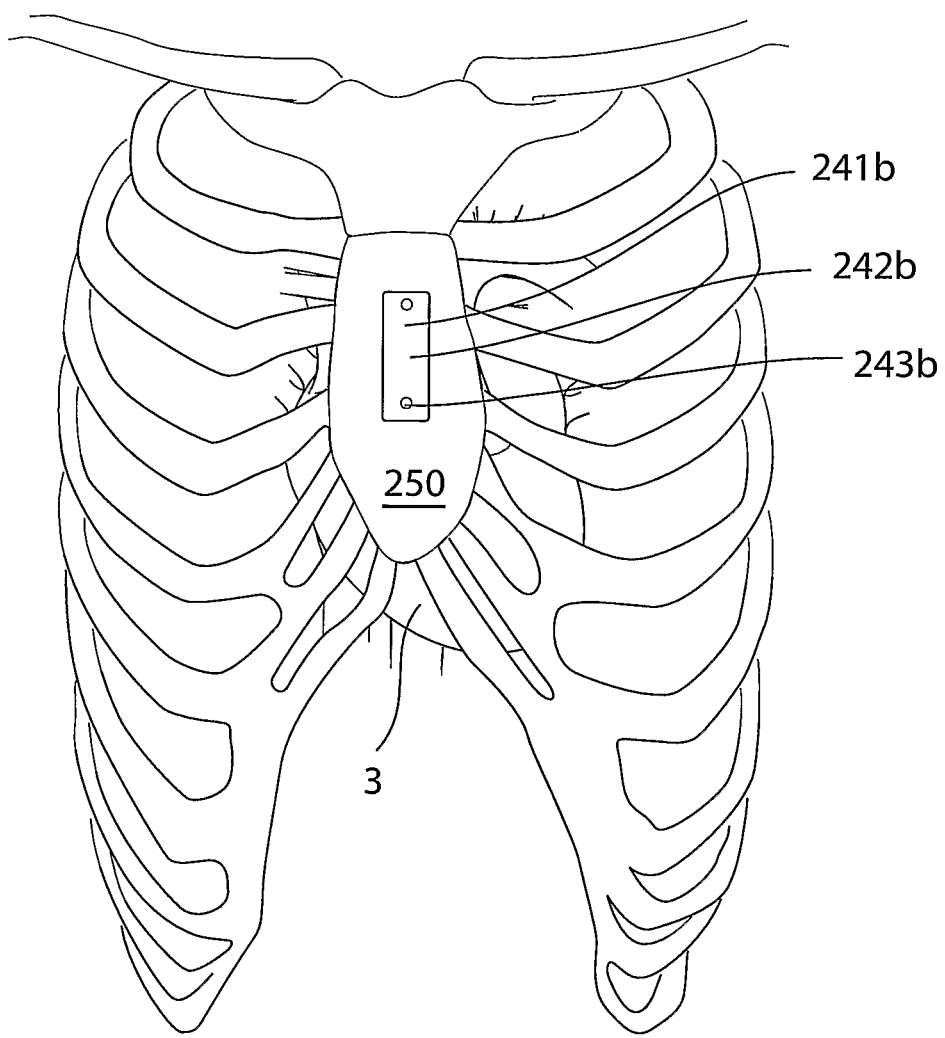
FIG. 21 shows a frontal view of the sternum of a human patient, with a fixating system applied.

FIG. 21 shows an embodiment where the heart pump apparatus 10 is adapted to be fixated to the sternum 250 of a human patient. The device is fixated using a fixating member 241b which is fixated to the sternum using screws 243. However the heart pump apparatus could be fixated to the sternum 250 of a human patient using any of the ways to place the fixating members described previously.

Figure 22:
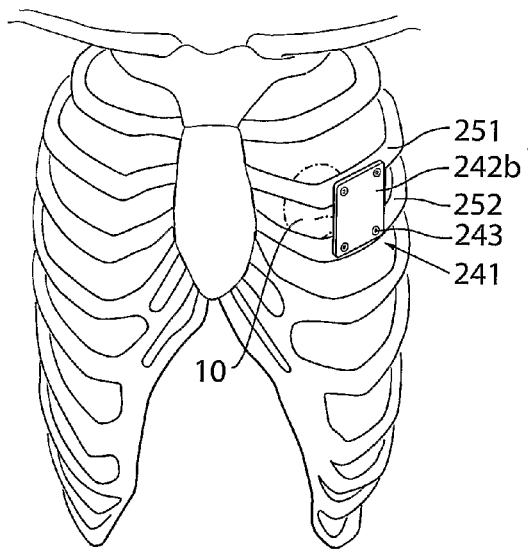
FIG. 22 shows a frontal view of the rib cage of a human patient, with a fixating system applied.

FIG. 22 shows an embodiment where the heart pump apparatus 10 is adapted to be fixated to two ribs 251, 252. A fixating member 241 comprising a plate 242b is fixated with screws adapted to fixate the fixating member to the cortex of the ribs.

Figure 23:
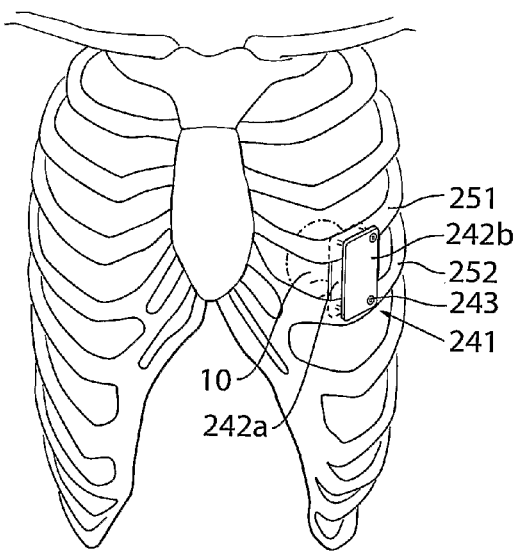
FIG. 23 shows a frontal view of the rib cage of a human patient, with a fixating system applied.

FIG. 23 shows an embodiment where the heart pump apparatus 10 is adapted to be fixated to two ribs 251, 252. A first plate 242a is provided on the posterior side of the rib cage, whereas a second plate 242b is provided in the anterior side of the rib cage. Screws 243 penetrate the ribs and fixates the first plate 242a to the second plate 242b. The tightening of the screws creates a clamping effect of the ribs 251,251 and provides the fixation of the heart pump apparatus 10. In another embodiment (not shown) the screws 243 are placed between the ribs 251,252 and that ways provides a clamping effect of the ribs 251,252.

Figure 24:
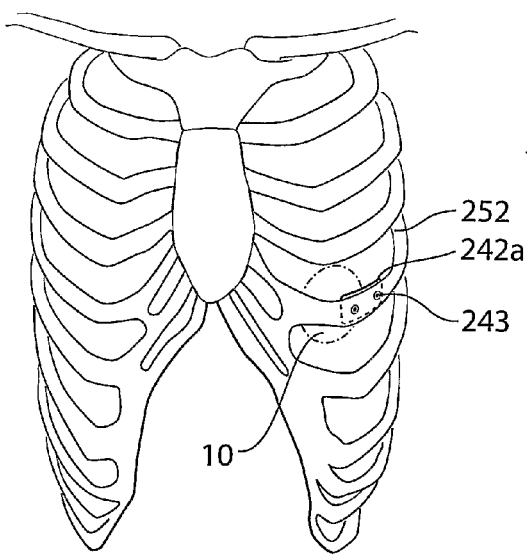
FIG. 24 shows a frontal view of the rib cage of a human patient, with a fixating system applied.

FIG. 24 shows an embodiment where the heart pump apparatus 10 is adapted to be fixated to one rib 252. A plate 242a is provided on the posterior side of the rib cage and screws 243 are provided from the outside thereof, penetrating the rib 252 and fixating the plate 242a to the rib 252.

Figure 25:
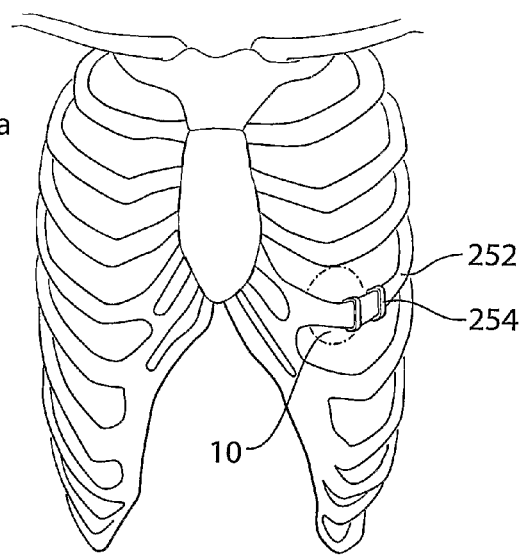
FIG. 25 shows a frontal view of the rib cage of a human patient, with a fixating system applied.

FIG. 25 shows an embodiment where the heart pump apparatus 10 is adapted to be fixated to one rib 252 using cord or band 254, this way there is no need to penetrate the rib 252. However the heart pump apparatus could be fixated to the ribcage of a human patient using any of the ways to place the fixating members described previously.

Figure 26:
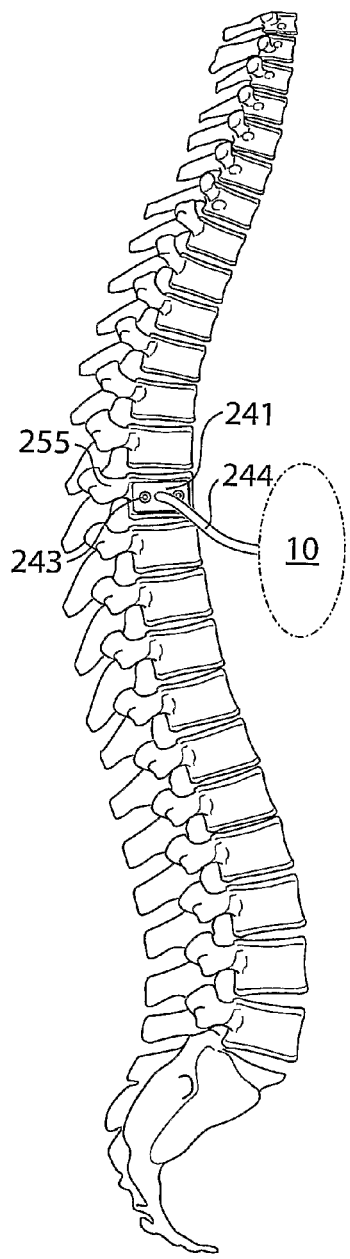
FIG. 26 shows a lateral view of the vertebral column of a human patient, with a fixating system applied.

FIG. 26 shows an embodiment where the heart pump apparatus 10 is adapted to be fixated to a vertebra 255 of the vertebral column. A fixating member 241 is fixated to the vertebra 255 using screws 243. The heart pump apparatus further comprises a connecting arm 244 that connects the heart pump apparatus 10 to the fixating member 241.

Figure 27:
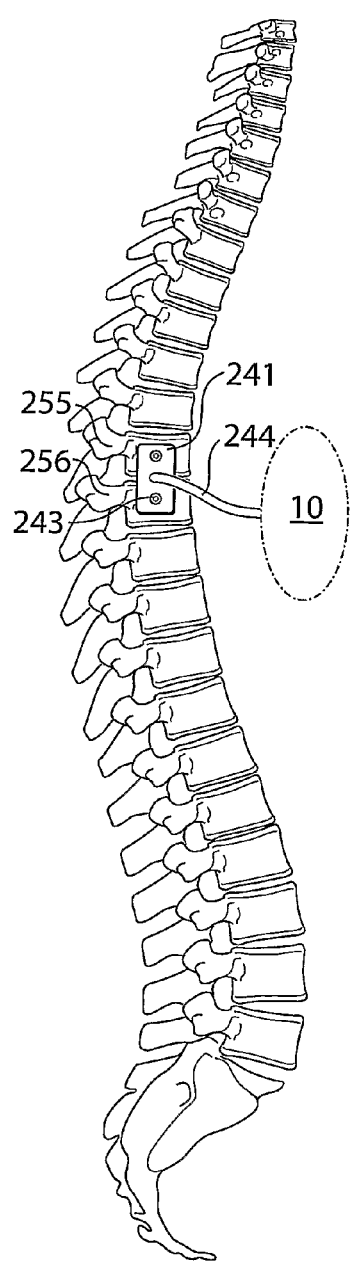
FIG. 27 shows a lateral view of the vertebral column of a human patient, with a fixating system applied.

FIG. 27 shows an embodiment where the heart pump apparatus 10 is adapted to be fixated to two vertebras 255, 256 of the vertebral column. A fixating member 241 is fixated to the two vertebras 255, 256 using screws 243. The heart pump apparatus further comprises a connecting arm 244 that connects the heart pump apparatus 10 to the fixating member 241.

Figure 28:
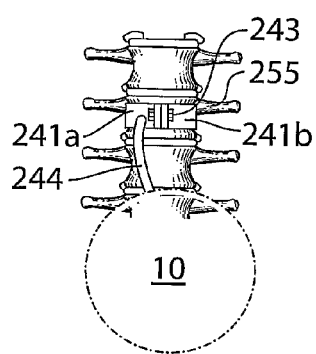
FIG. 28 shows a frontal view of a part of the vertebral column of a human patient, with a fixating system applied.

FIG. 28 shows an embodiment where the heart pump apparatus is adapted to be fixated to a vertebra 255 of the vertebral column by clamping said vertebra 255. Two fixating members 241a, 241b is placed on two sides of the vertebra and an attachment comprising screws 243 clamps the vertebra between the first and second fixating members 241a,b. The heart pump apparatus further comprises a connecting connecting arm 244 that connects the heart pump apparatus 10 to the fixating member 241.

In all of the above mentioned embodiments the means of attachment could be replaced with other mechanical attachments or an adhesive. Other mechanical attachments suitable could be: pop-rivets, nails, staples, band or cord. The mechanical fixating members could be of a metallic or ceramic material. Suitable metallic materials could be titanium or surgical steel.

Figure 29:
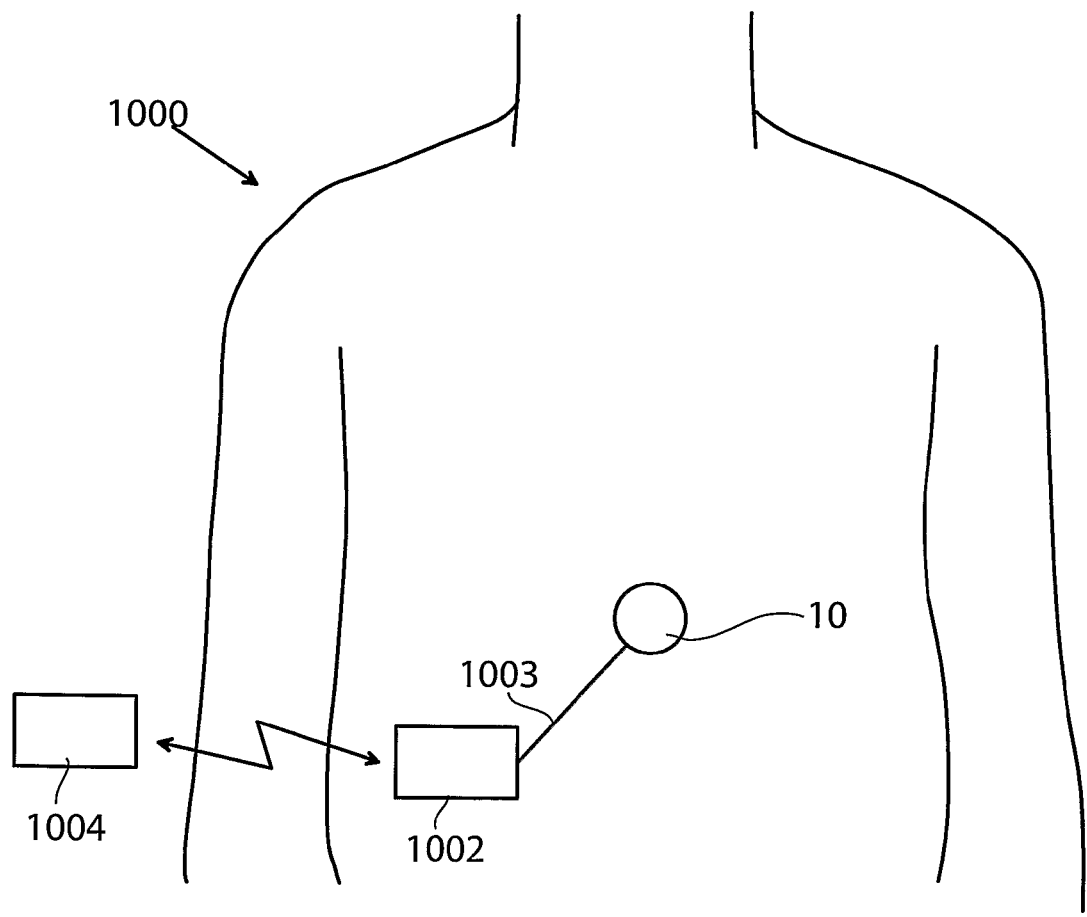
FIG. 29 illustrates a system for treating a disease, wherein the system includes an apparatus of the invention implanted in a patient.

FIG. 29 illustrates a system for treating a disease comprising an apparatus 10 of the present invention placed in the abdomen of a patient. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The implanted energy-transforming device 1002 may also comprise other components, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal. The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Figure 30:
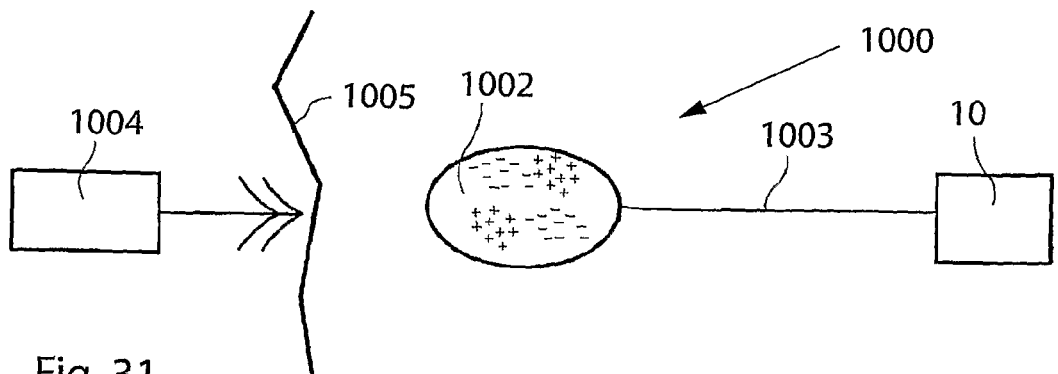
FIGS. 30-44 schematically show various embodiments of the system for wirelessly powering the apparatus shown in FIG. 1.

FIG. 30 illustrates the system of FIG. 29 in the form of a more generalized block diagram showing the apparatus 10, the energy-transforming device 1002 powering the apparatus 10 via power supply line 1003, and the external energy-transmission device 1004, The patient's skin 1005, generally shown by a vertical line, separates the interior of the patient to the right of the line from the exterior to the left of the line.

Figure 31:
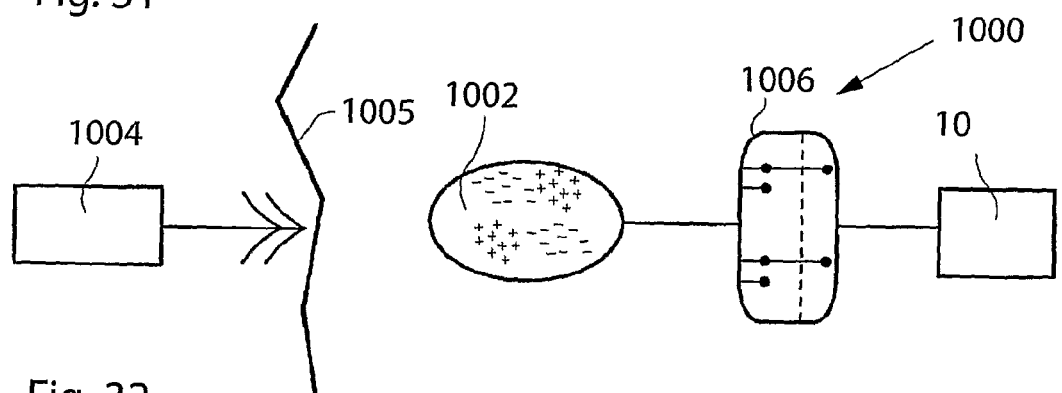

FIG. 31 shows an embodiment of the invention identical to that of FIG. 30, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

Figure 32:
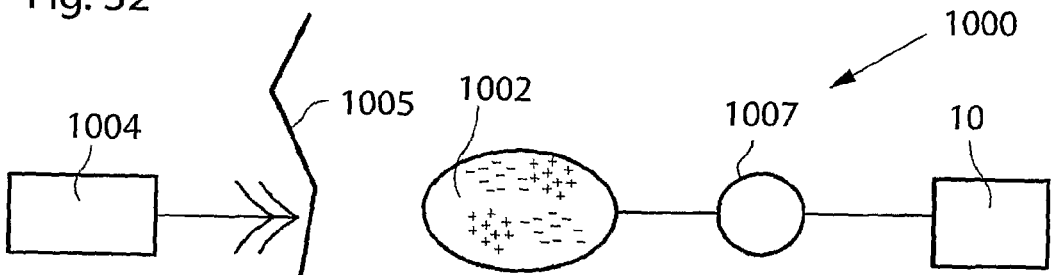

FIG. 32 shows an embodiment of the invention identical to that of FIG. 30, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

Figure 33:
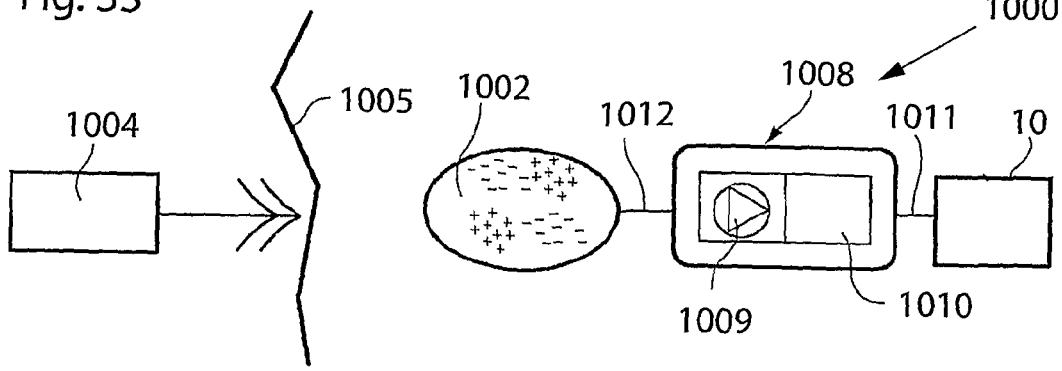

FIG. 33 shows an embodiment of the invention identical to that of FIG. 30, except that it also comprises an operation device is in the form of an assembly 1008 including a motor/pump unit 1009 and a fluid reservoir 1010 is implanted in the patient. In this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 34:
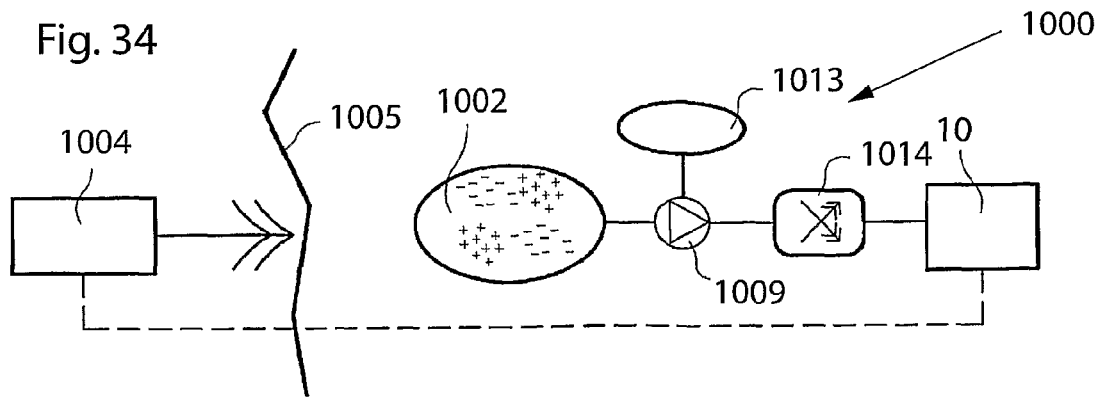

FIG. 34 shows an embodiment of the invention comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

Figure 35:
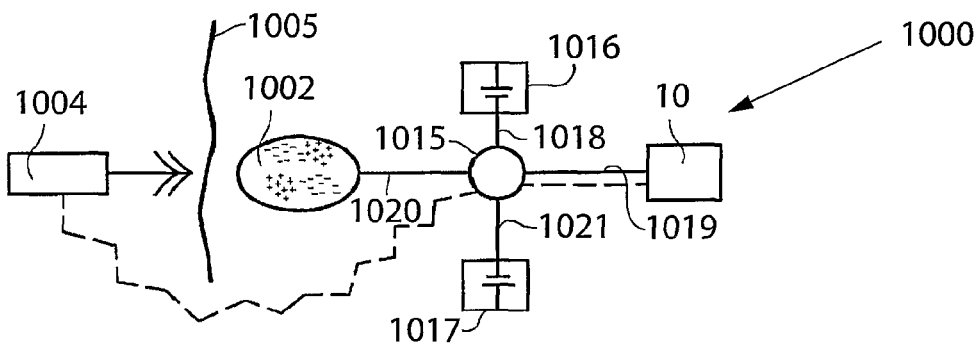

FIG. 35 shows an embodiment of the invention comprising the external energy-transmission device 1004 with its wireless remote control, the apparatus 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

Figure 7:
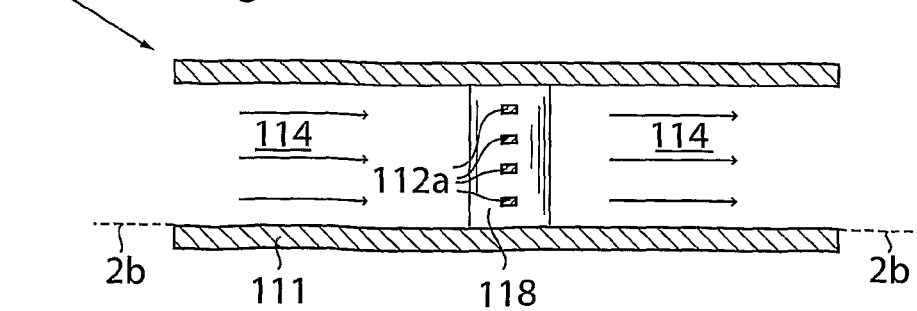
FIG. 7 is a sectional view of the clot removal device of FIG. 5 taken along the line IV-IV.

In accordance with an alternative, the capacitor 1017 in the embodiment of FIG. 7 may be omitted. In accordance with another alternative, the accumulator 1016 in this embodiment may be omitted.

Figure 36:
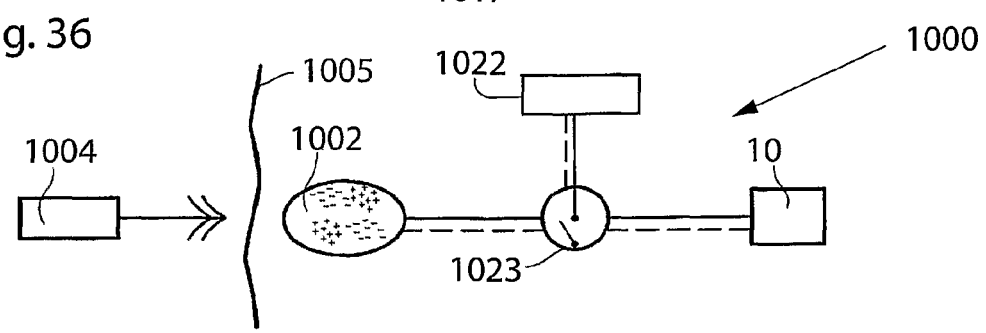
Figure 63:
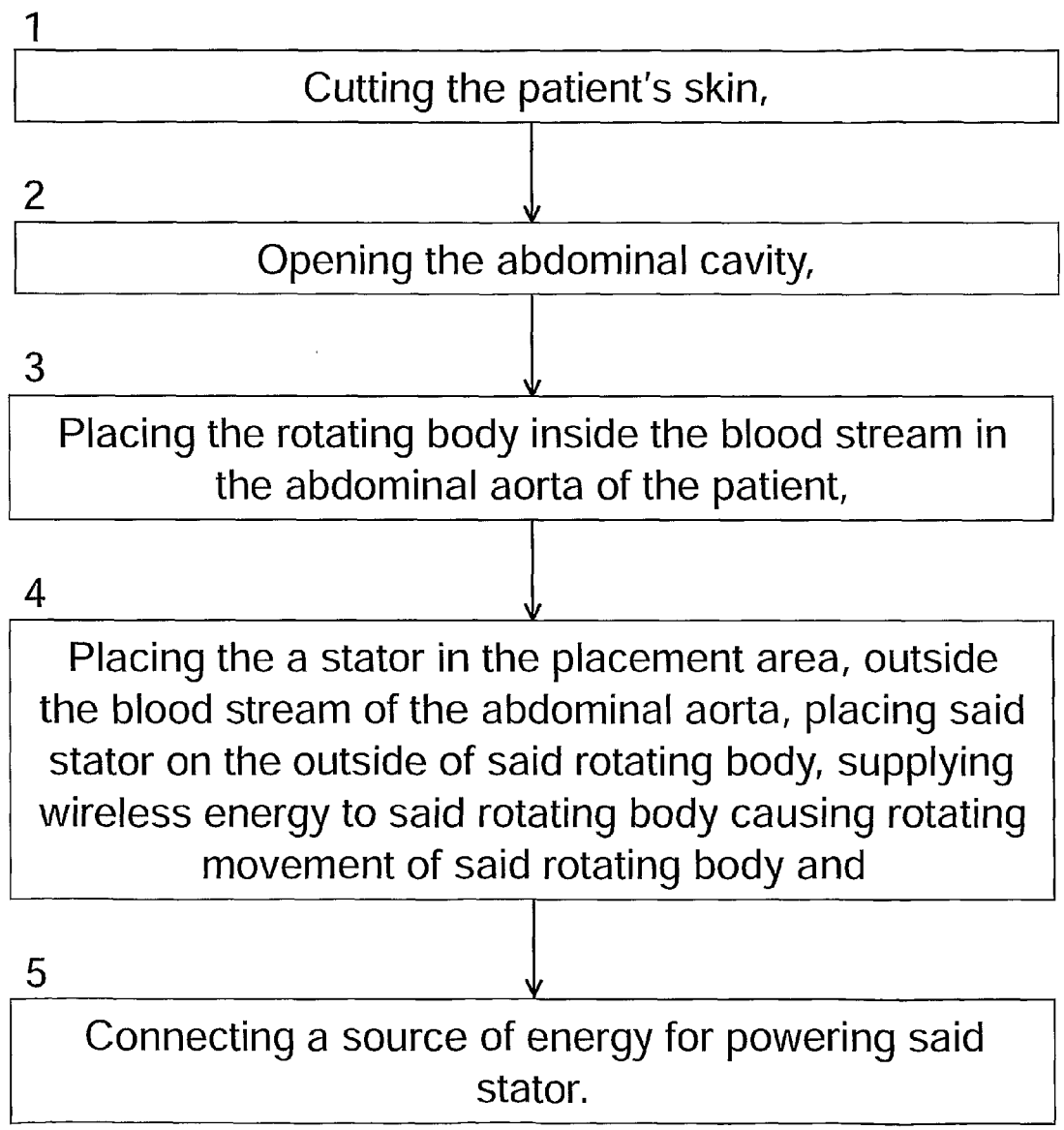

FIG. 36 shows an embodiment of the invention identical to that of FIG. 63, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 37:
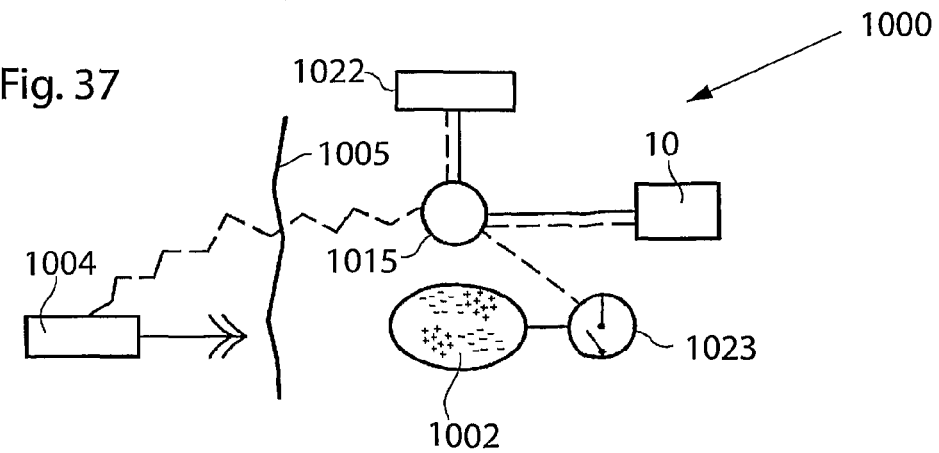

FIG. 37 shows an embodiment of the invention identical to that of FIG. 69, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 38:
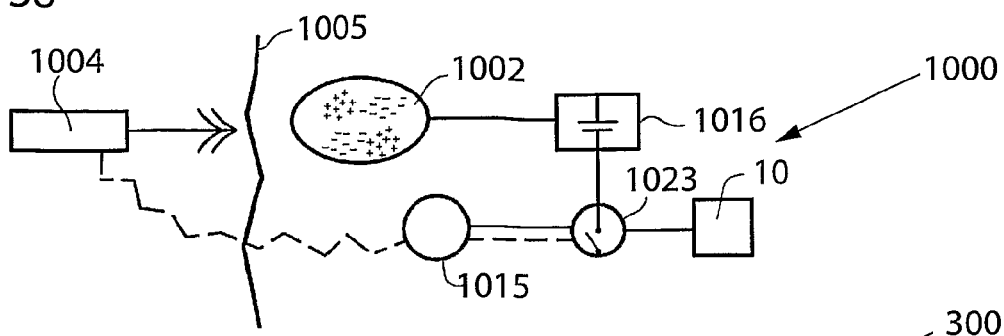

FIG. 38 shows an embodiment of the invention identical to that of FIG. 37, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 39:
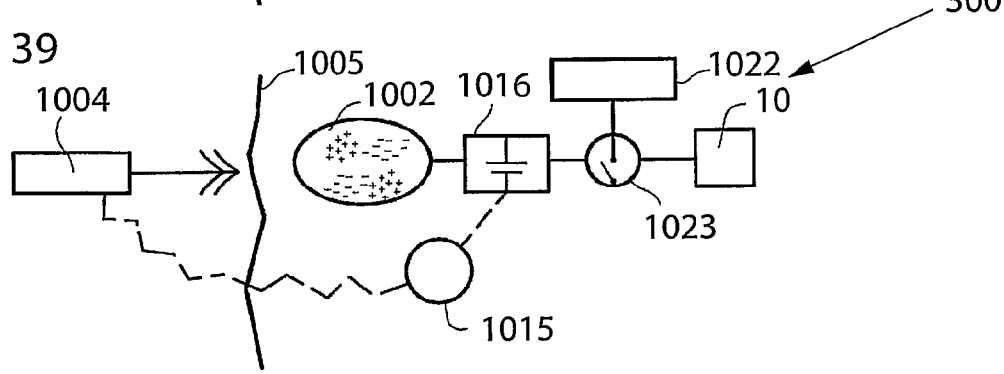

FIG. 39 shows an embodiment of the invention identical to that of FIG. 38, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 40:
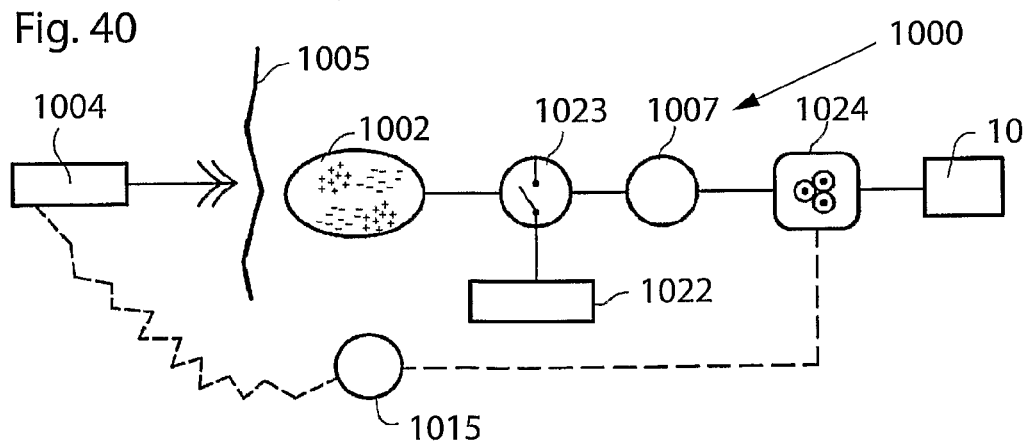

FIG. 40 shows an embodiment of the invention identical to that of FIG. 36, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 41:
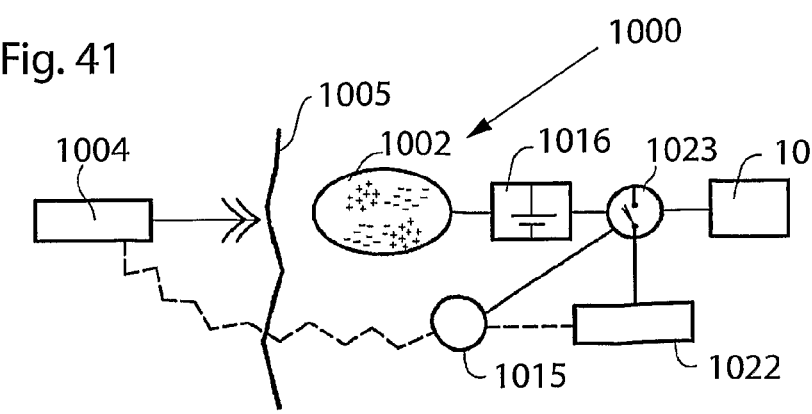

FIG. 41 shows an embodiment of the invention identical to that of FIG. 40 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

Figure 42:
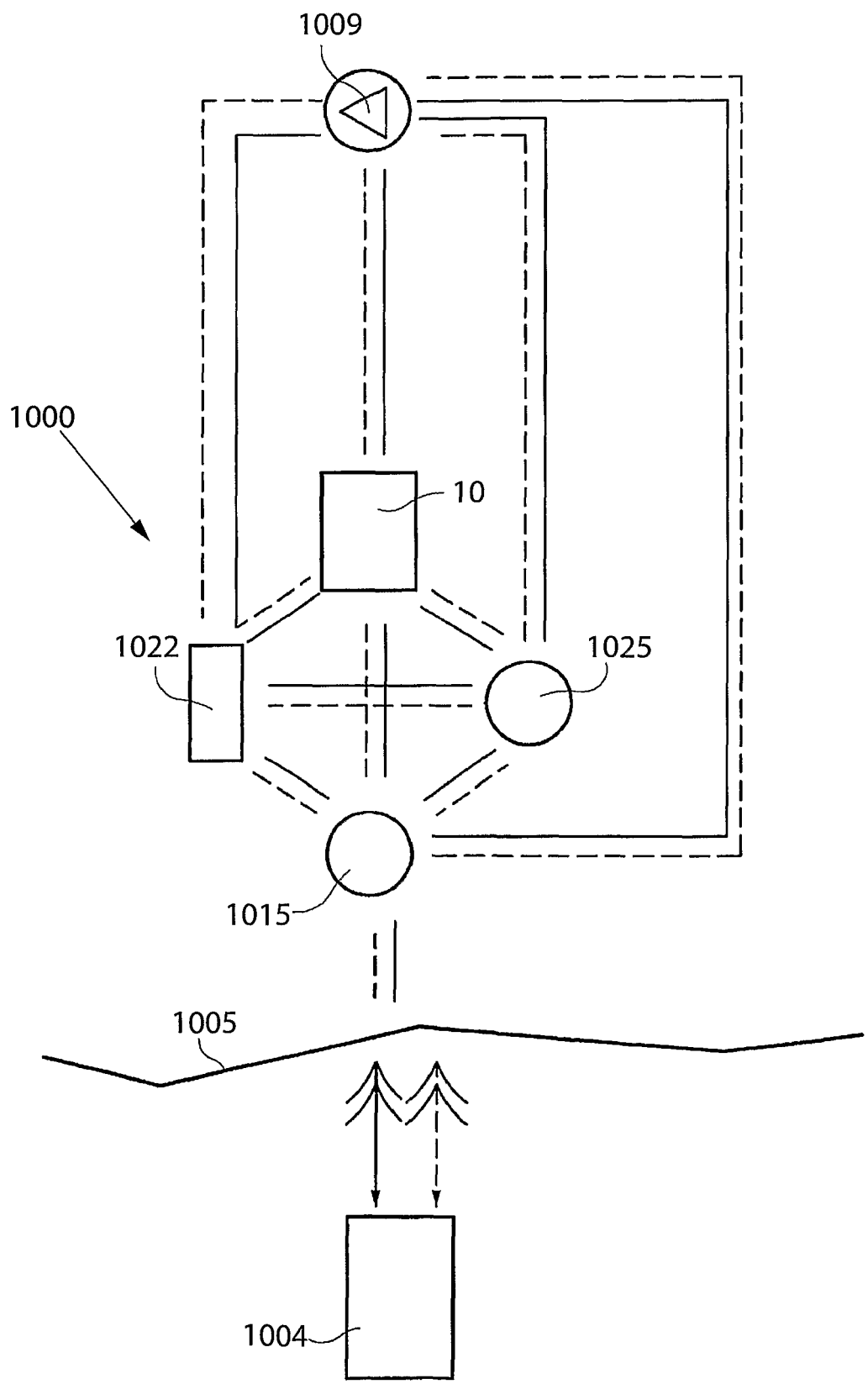

FIG. 42 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 43:
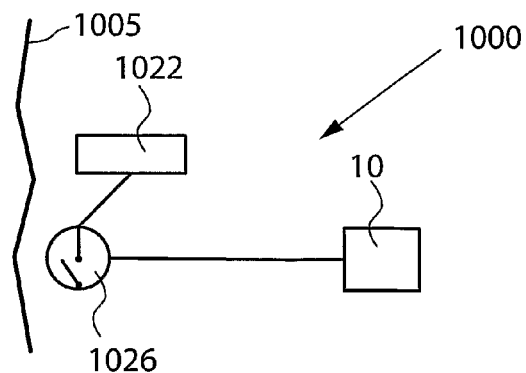

FIG. 43 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 44:
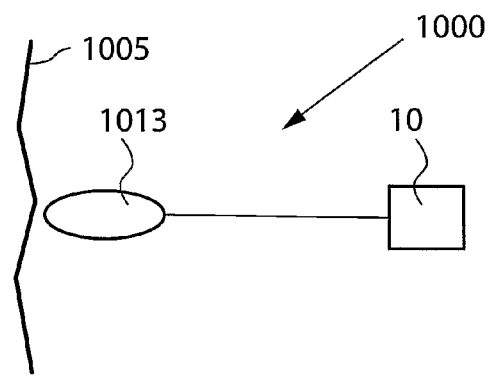

FIG. 44 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 45:
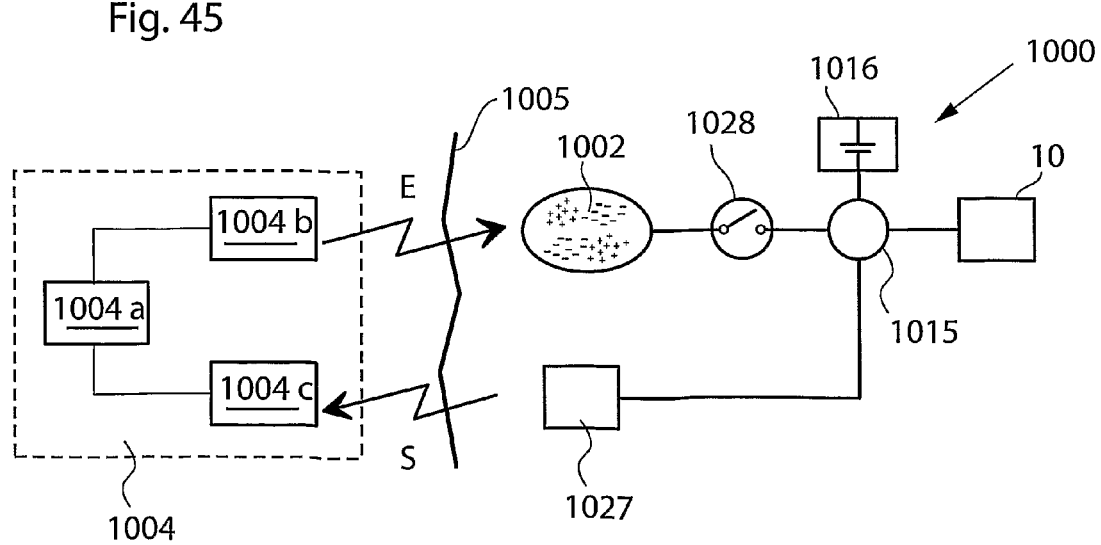
FIG. 45 is a schematic block diagram illustrating an arrangement for supplying an accurate amount of energy used for the operation of the apparatus shown in FIG. 1.

FIG. 45 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 45 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004*b*. The energy balance and the currently required amount of energy can then be determined by the external control unit 1004*b* based on those sensor measurements.

Hence, the present solution according to the arrangement of FIG. 45 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 45, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 45 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 46:
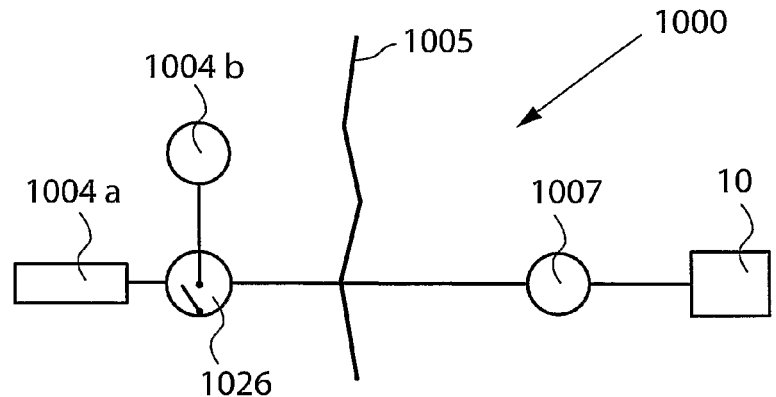
FIG. 46 schematically shows an embodiment of the system, in which the apparatus is operated with wire bound energy.

With reference to FIG. 46, although wireless transfer of energy for operating the apparatus has been described above to enable non-invasive operation, it will be appreciated that the apparatus can be operated with wire bound energy as well. Such an example is shown in FIG. 46, wherein an external switch 1026 is interconnected between the external energy source 1004*a* and an operation device, such as an electric motor 1007 operating the apparatus 10. An external control unit 1004*b* controls the operation of the external switch 1026 to effect proper operation of the apparatus 10.

Figure 47:
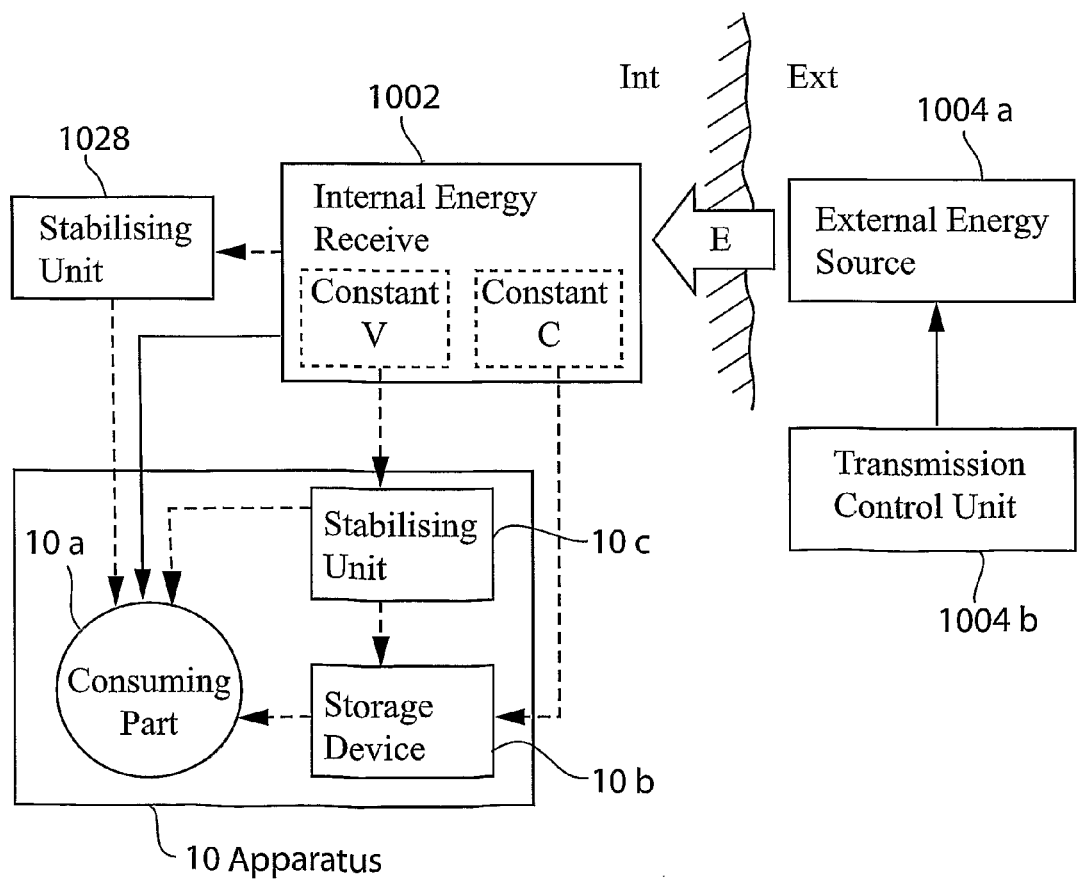
FIG. 47 is a more detailed block diagram of an arrangement for controlling the transmission of wireless energy used for the operation of the apparatus shown in FIG. 1.

FIG. 47 illustrates different embodiments for how received energy can be supplied to and used by the apparatus 10. Similar to the example of FIG. 45, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 1002. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 45 and FIG. 47 illustrate some possible but non-limiting implementation options regarding how the various shown functional components and elements can be arranged and connected to each other. However, the skilled person will readily appreciate that many variations and modifications can be made within the scope of the present invention.

Figure 48:
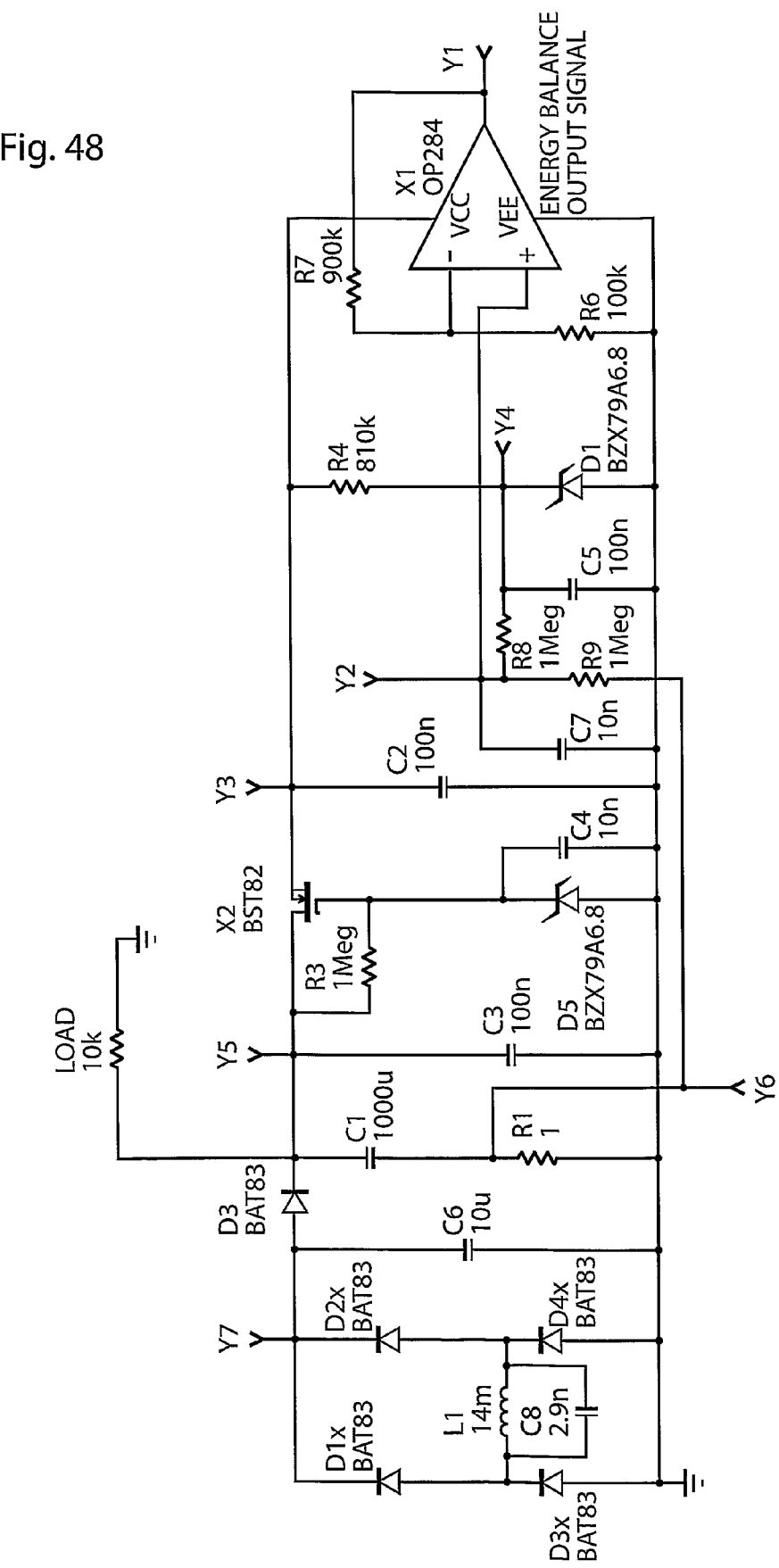
FIG. 48 is a circuit for the arrangement shown in FIG. 29, according to a possible implementation example.

FIG. 48 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 48 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 31; the transmitting parts of the system are excluded.

The implementation of the general concept of energy balance and the way the information is transmitted to the external energy transmitter can of course be implemented in numerous different ways. The schematic FIG. 48 and the above described method of evaluating and transmitting the information should only be regarded as examples of how to implement the control system.

Circuit Details

In FIG. 48 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 31 could be incorporated in any of the embodiments of FIGS. 34-40, the hydraulic valve shifting device 1014 of FIG. 34 could be incorporated in the embodiment of FIG. 33, and the gear box 1024 could be incorporated in the embodiment of FIG. 32. Please observe that the switch simply could mean any electronic circuit or component.

The embodiments described in connection with FIGS. 45, 47 and 48 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming components of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.
- The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
- The energy used for the apparatus is consumed to operate the apparatus, and/or stored in at least one energy storage device of the apparatus.
- Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.
- When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.
- When the derivative is determined over time of a measured electrical parameter related to the amount of consumed and/or stored energy, the determination device determines the derivative for a monitored voltage and/or current related to the energy balance.
- The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 49-52 show in more detail block diagrams of four different ways of hydraulically or pneumatically powering an implanted apparatus according to the invention.

Figure 49:
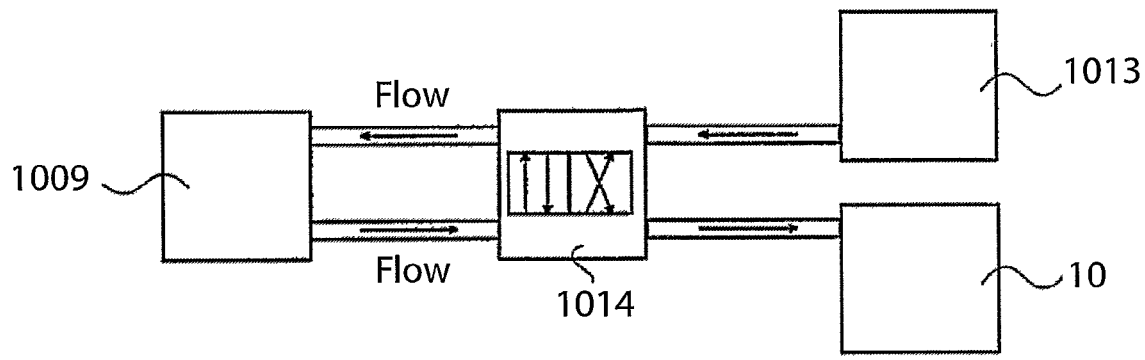
FIGS. 49-55 show various ways of arranging hydraulic or pneumatic powering of an apparatus implanted in a patient.

FIG. 49 shows a system as described above with. The system comprises an implanted apparatus 10 and further a separate regulation reservoir 1013, a one way pump 1009 and an alternate valve 1014.

Figure 50:
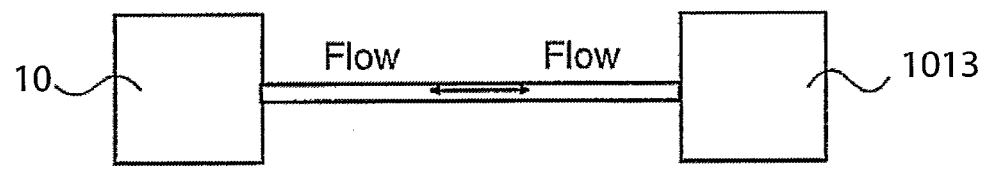

FIG. 50 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 51:
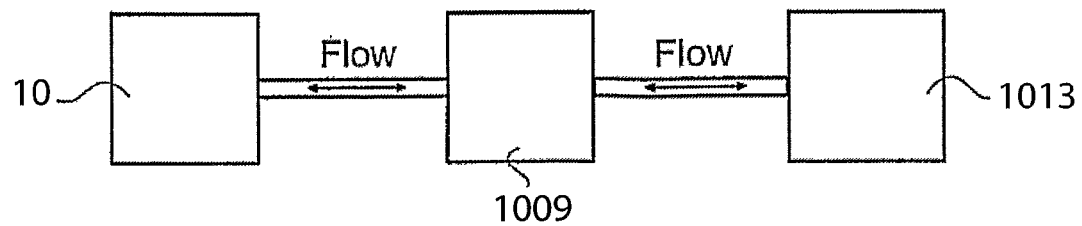

FIG. 51 shows the apparatus 10, a two way pump 1009 and the regulation reservoir 1013.

Figure 52:
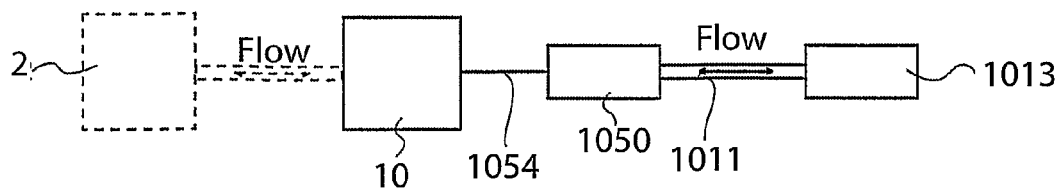

FIG. 52 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

Figure 53A:
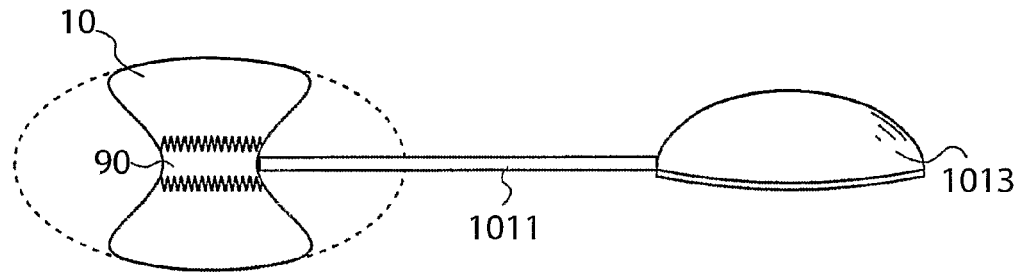
Figure 53B:
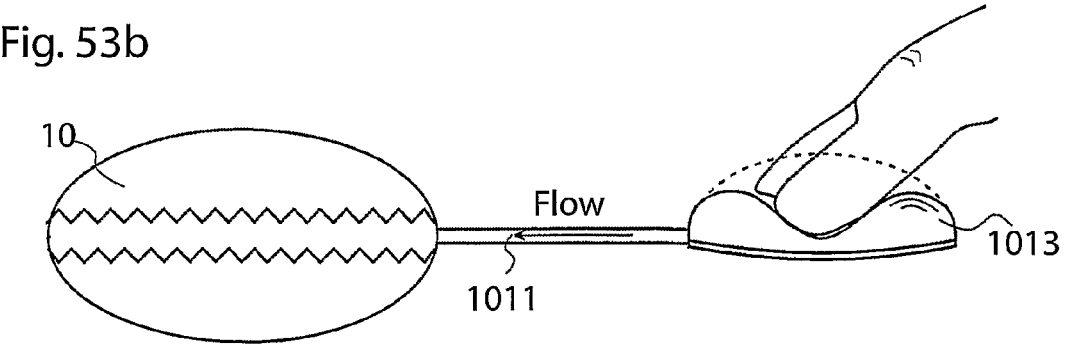
Figure 53C:
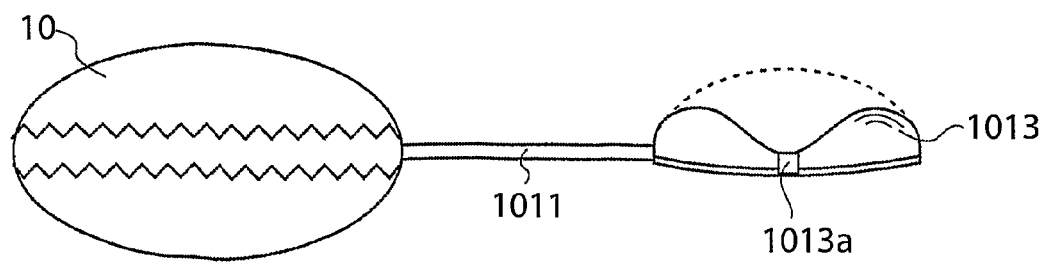
Figure 54:
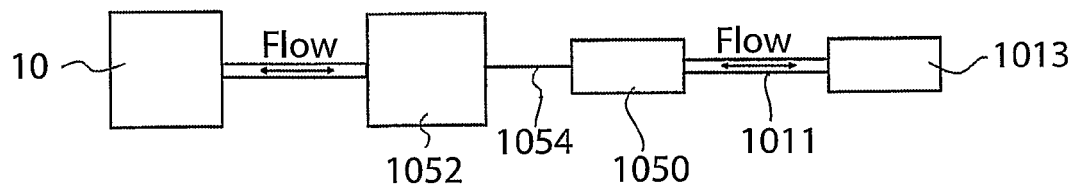

In one embodiment, the regulation reservoir is placed subcutaneous under the patient's skin and is operated by pushing the outer surface thereof by means of a finger. This system is illustrated in FIGS. 53a-c. In FIG. 53a, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 53a, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 53b shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 54 and 55a-c. The block diagram shown in FIG. 54 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 55A:
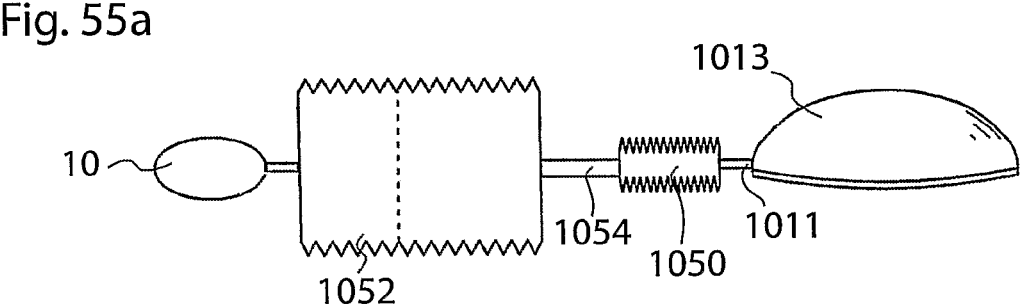
Figure 55B:
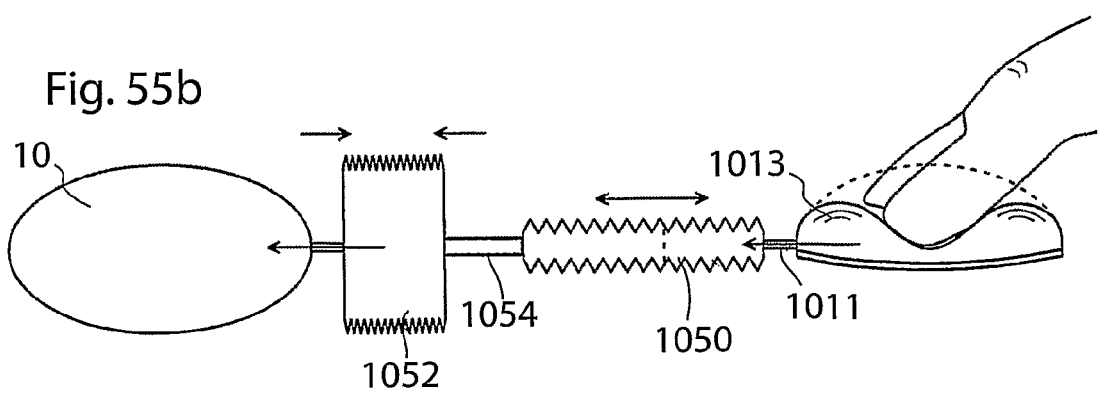
Figure 55C:
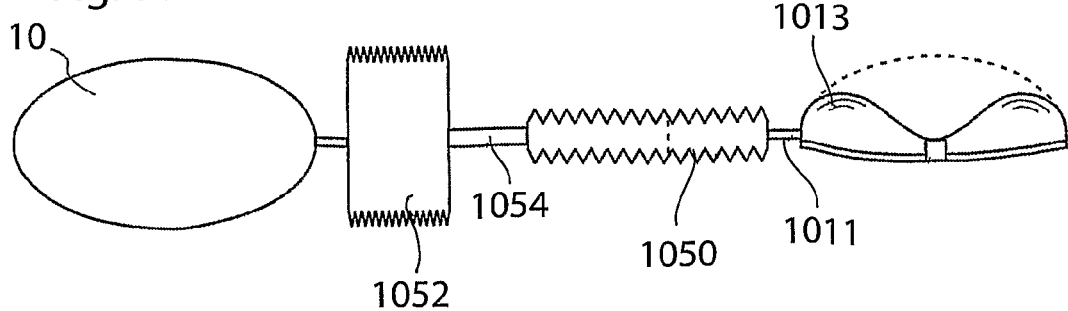

An example of this embodiment will now be described with reference to FIG. 55a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 55a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 53a-c, the regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Figure 56:
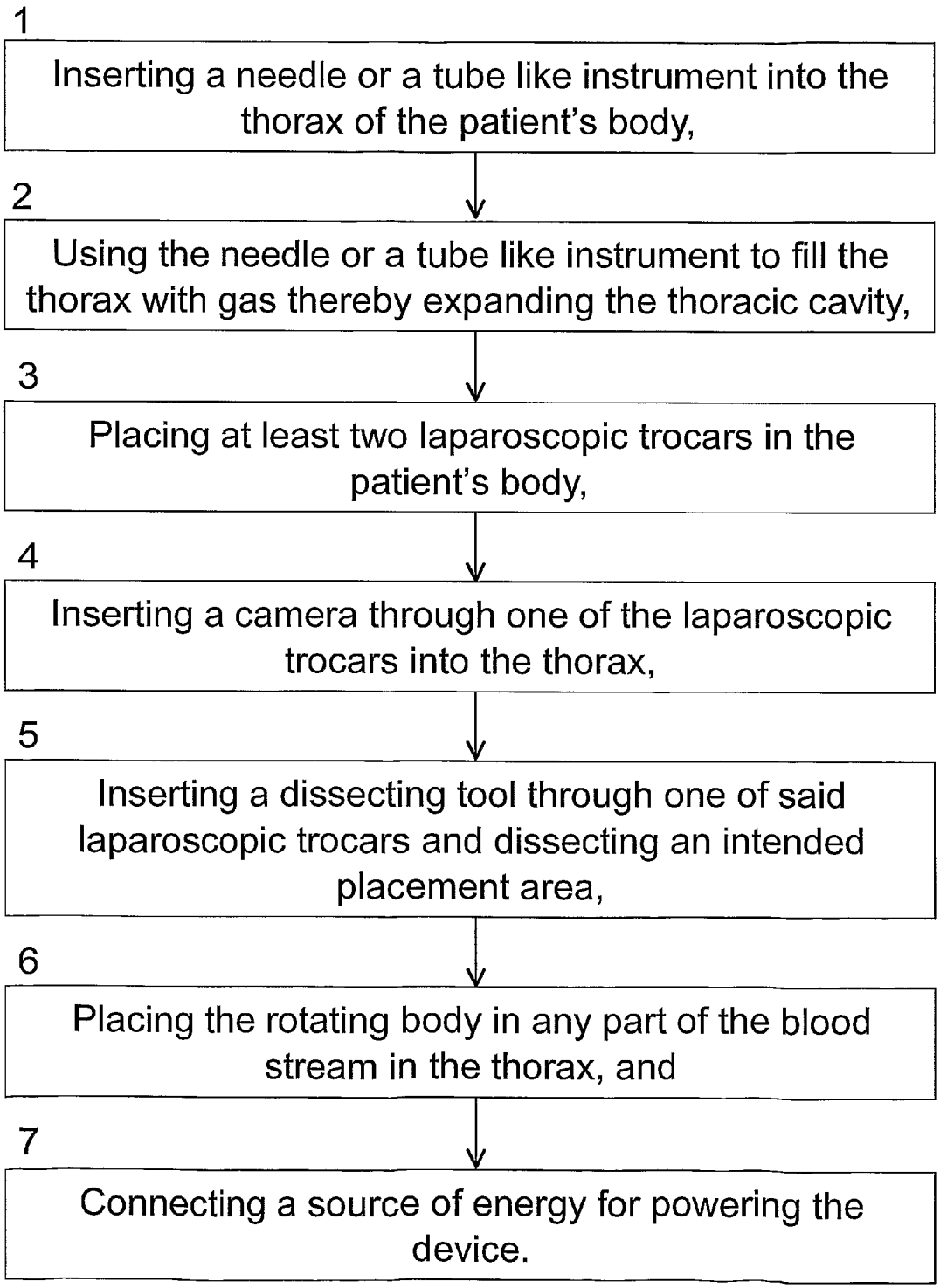

FIG. 56 shows a flow chart of an operation method comprising the steps of:
1. Inserting a needle or tube like instrument into the thorax of the patient's body.
2. Using the needle or tube like instrument to fill the thorax with gas, thereby expanding the thoracic cavity.
3. Placing at least two laparoscopic trocars in the patient's body.
4. Inserting a camera through one of the laparoscopic trocars into the thorax.
5. Inserting a dissecting tool through one of the laparoscopic trocars and dissecting an intended placement area.
6. Placing the rotating body in any part of the blood stream in the thorax.
7. Connecting a source of energy for powering the device.

The method of the flow chart is also described with reference to FIG. 4b. The area of dissection can of course be varied since the placing of the drive unit should be performed such that the drive unit is placed in magnetic connection with the rotating body 18. The following descriptions with reference to flow charts of FIGS. 57-65 also describes operational methods with slight variations. However, the steps of these methods could be exchanged within or between the methods to adapt the method ti a particular procedure.

Figure 57:
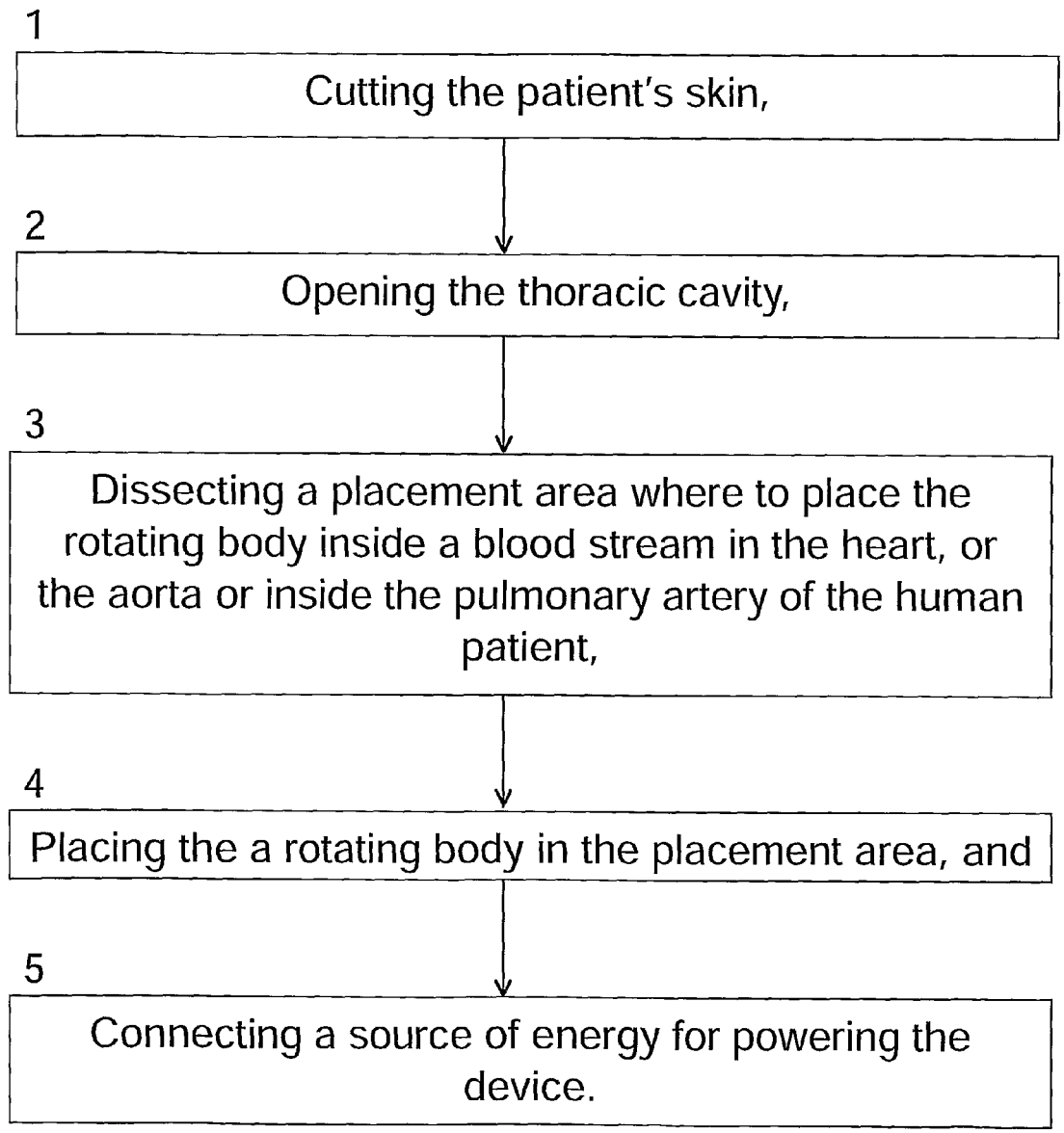

FIG. 57 shows a flow chart of an operation method comprising the steps of:
1. Cutting the skin of a patient.
2. Opening the thoracic cavity.
3. Dissecting a placement area where to place the rotating body inside a blood stream in the heart, or the aorta or inside the pulmonary artery of the patient.
4. Placing the rotating body in the placement area, and
5. Connecting a source of energy for powering the device.

FIG. 58 shows a flow chart of an operation method comprising the steps of:
1. Inserting a needle or tube like instrument into the abdomen of the patient's body.
2. Using the needle or tube like instrument to fill the abdomen with gas, thereby expanding the abdominal cavity.
3. Placing at least two laparoscopic trocars in the patient's body.
4. Inserting a camera through one of the laparoscopic trocars into the abdomen.
5. Inserting a dissecting tool through one of the laparoscopic trocars and dissecting an intended placement area.
6. Placing the rotating body in any part of the blood stream in the abdominal aorta.
7. Connecting a source of energy for powering the device.

Figure 59:
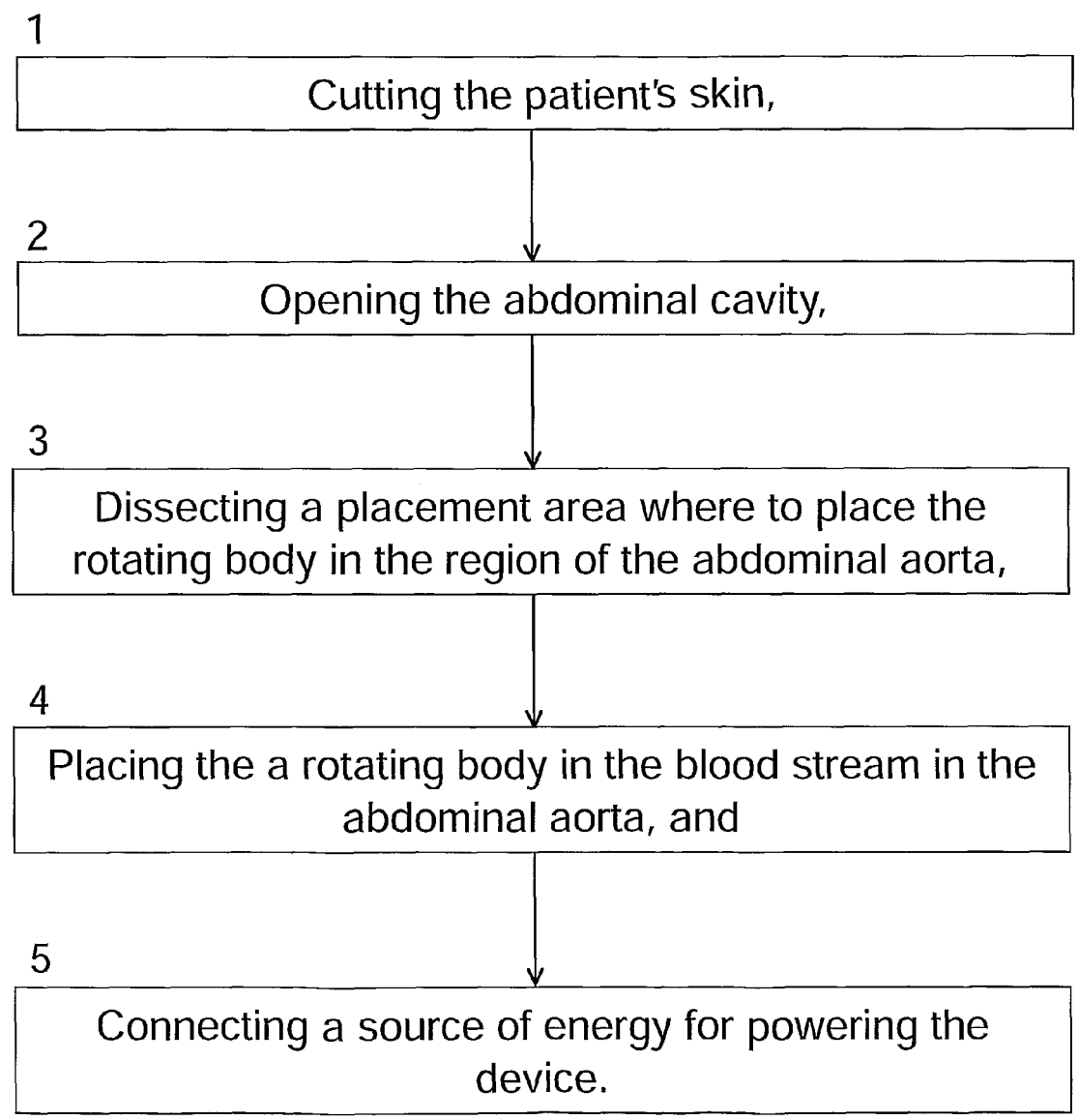

FIG. 59 shows a flow chart of an operation method comprising the steps of:
1. Cutting the skin of a patient.
2. Opening the abdominal cavity.
3. Dissecting a placement area where to place the rotating body in the region of the abdominal aorta of the patient.
4. Placing the rotating body in the blood stream in the abdominal aorta, and
5. Connecting a source of energy for powering the device.

FIG. 60 shows a flow chart of an operation method comprising the steps of:
1. Inserting a needle or tube like instrument into the thorax of the patient's body.
2. Using the needle or tube like instrument to fill the thorax with gas, thereby expanding the thoracic cavity.
3. Placing at least two laparoscopic trocars in the patient's body.
4. Inserting a camera through one of the laparoscopic trocars into the thorax.
5. Inserting at least one dissecting tool through one of the laparoscopic trocars and dissecting an intended placement area in the vascular system of the patient.
6. Placing the rotating body in any part of the blood stream in the thorax, inside a blood stream of the blood vessel in the heart, or the aorta or inside the pulmonary artery of the patient.
7. Placing a stator in the placement area, outside the blood stream of the blood vessel, outside the heart, or the aorta or outside the pulmonary artery of the patient, placing said stator on the outside of the rotating body, supplying wireless energy to the rotating body causing rotating movement of the rotating body.
8. Connecting a source of energy for powering the stator.

Figure 61:
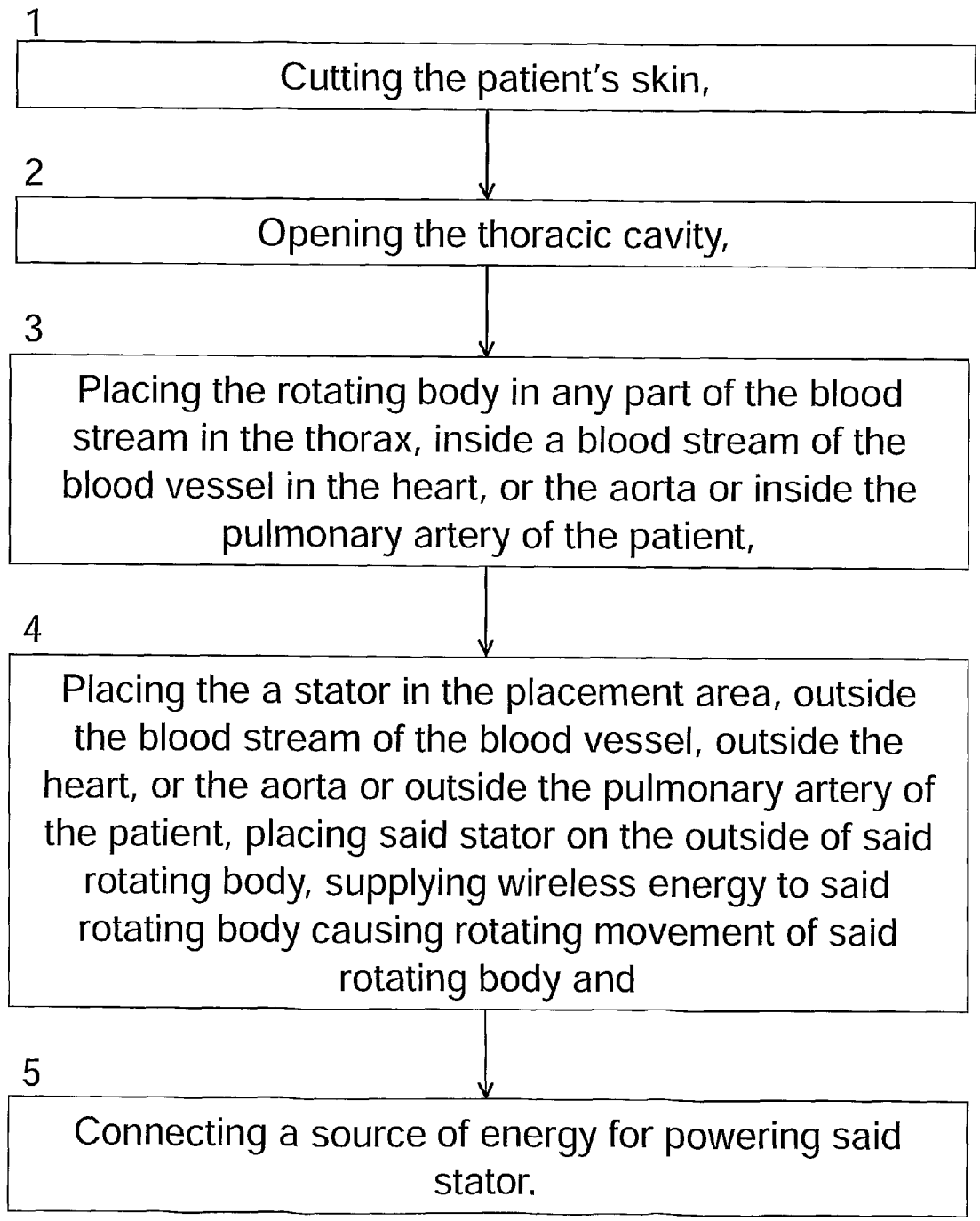

FIG. 61 shows a flow chart of an operation method comprising the steps of:
1. Cutting the skin of a patient.
2. Opening the abdominal cavity.
3. Placing the rotating body in any part of the blood stream in the thorax, inside a blood stream of the blood vessel in the heart, or the aorta or inside the pulmonary artery of the patient.
4. Placing a stator in the placement area, outside the blood stream of the blood vessel, outside the heart, or the aorta or outside the pulmonary artery of the patient, placing said stator on the outside of the rotating body, supplying wireless energy to the rotating body causing rotating movement of the rotating body.
5. Connecting a source of energy for powering the stator.

Figure 62:
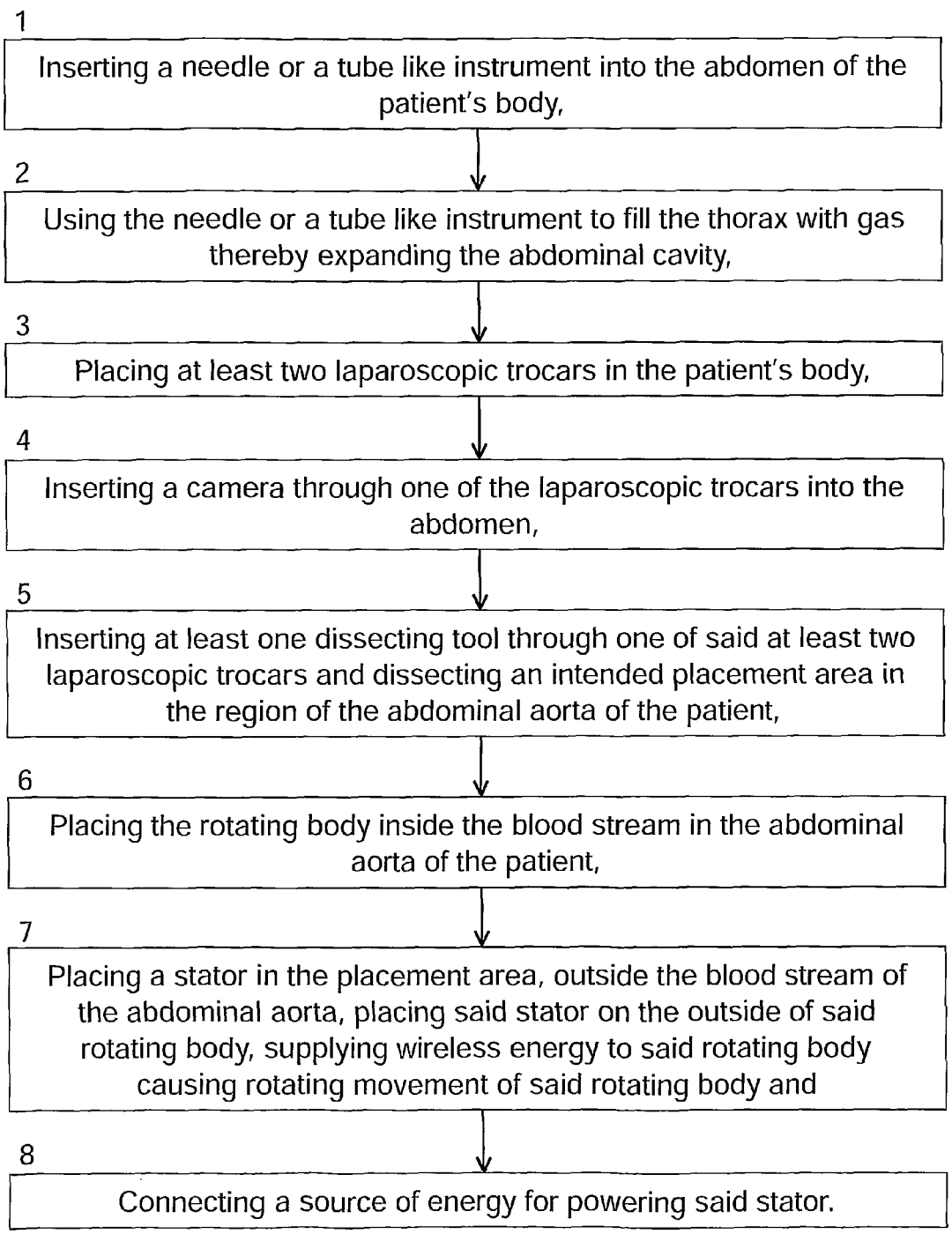

FIG. 62 shows a flow chart of an operation method comprising the steps of:
1. Inserting a needle or tube like instrument into the abdomen of the patient's body.
2. Using the needle or tube like instrument to fill the abdomen with gas, thereby expanding the abdominal cavity.
3. Placing at least two laparoscopic trocars in the patient's body.
4. Inserting a camera through one of the laparoscopic trocars into the abdomen.
5. Inserting at least one dissecting tool through one of the laparoscopic trocars and dissecting an intended placement area in the region of the abdominal aorta of the patient.
6. Placing the rotating body inside the blood stream in the abdominal aorta of the patient.
7. Placing a stator in the placement area, outside the blood stream of the abdominal aorta, placing the stator on the outside of the rotating body, supplying wireless energy to the rotating body causing rotating movement of the rotating body.
8. Connecting a source of energy for powering the stator.

FIG. 63 shows a flow chart of an operation method comprising the steps of:
1. Cutting the skin of a patient.
2. Opening the abdominal cavity.
3. Placing the rotating body in any part of the blood stream in the abdominal aorta of the patient.

4. Placing a stator in the placement area, outside the blood stream of the abdominal aorta, placing the stator on the outside of the rotating body, supplying wireless energy to the rotating body causing rotating movement of the rotating body.

5. Connecting a source of energy for powering the stator.

Figure 64:
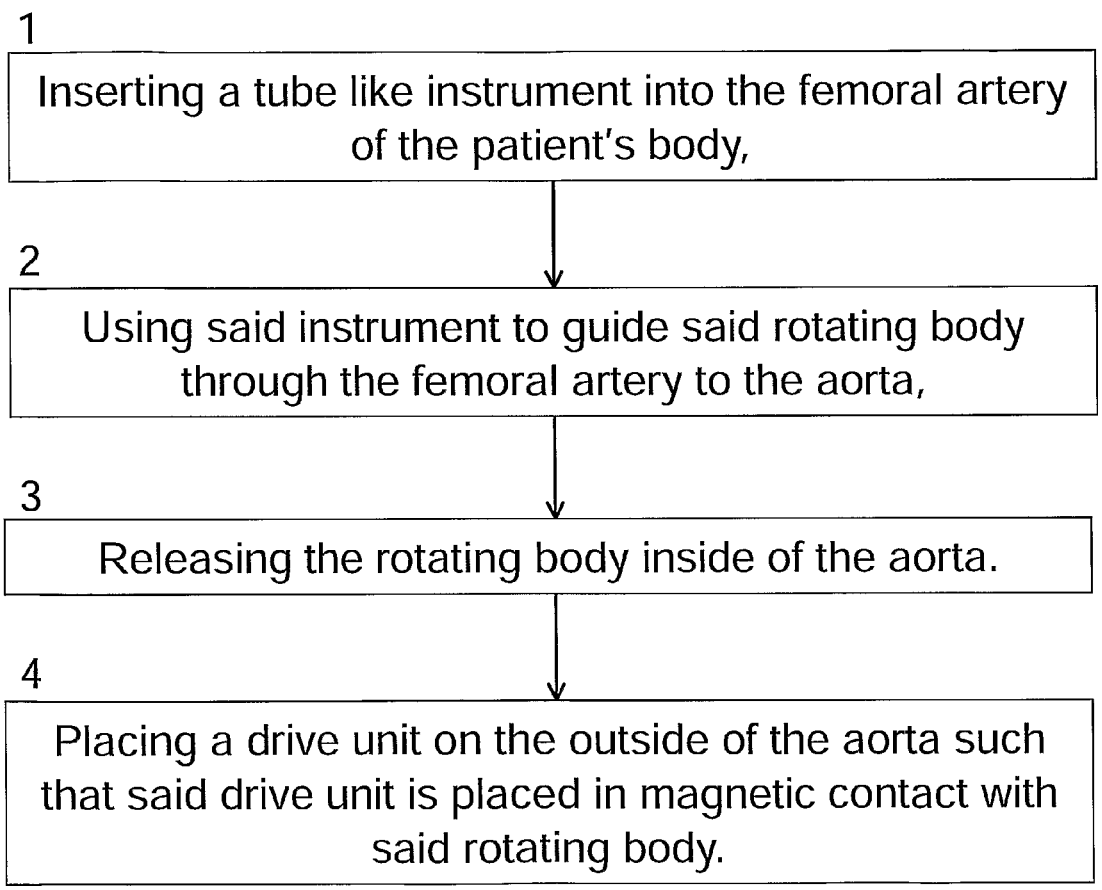

FIG. 64 shows a flow chart of an operation method comprising the steps of:
1. Inserting a tube like instrument into the femoral artery of the patient's body.
2. Using the instrument to guide the rotating body through the femoral artery to the aorta.
3. Releasing the rotating body inside of the aorta.
4. Placing a drive unit on the outside of the aorta such that the drive unit is placed in magnetic contact with the rotating body.

Figure 65:
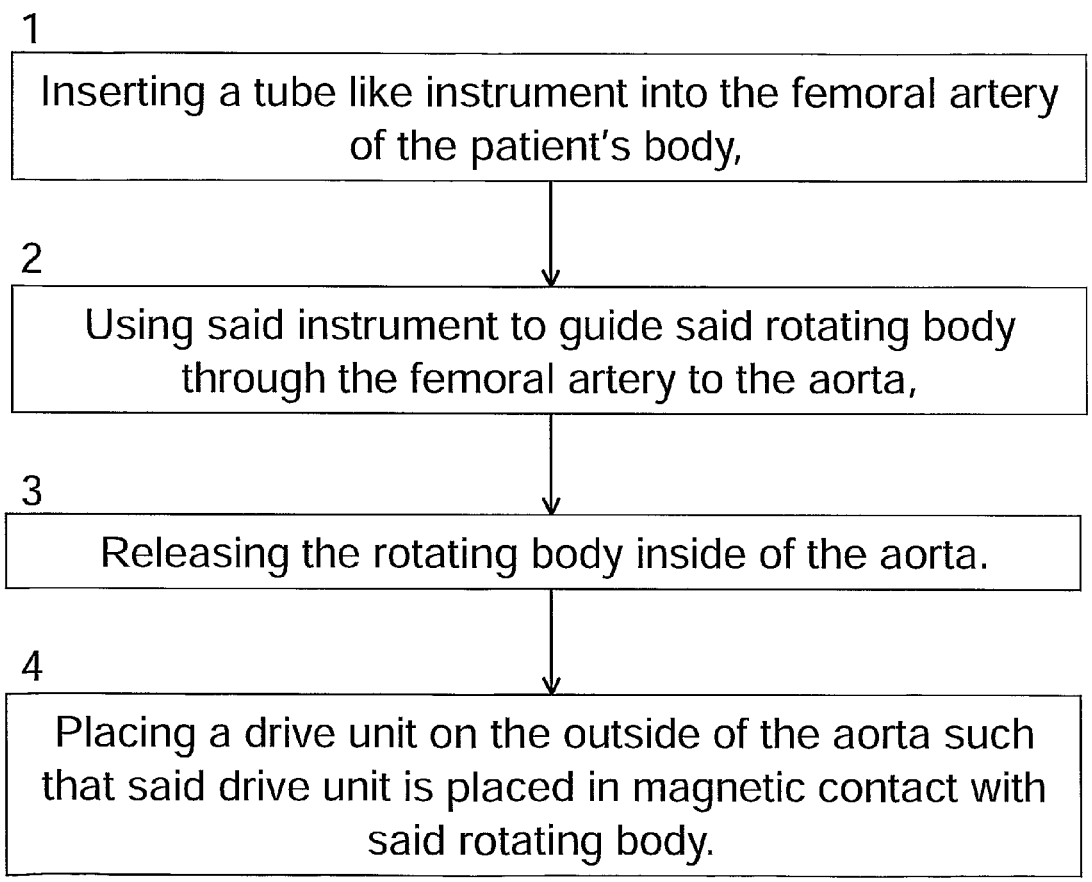

FIG. 65 shows a flow chart of an operation method comprising the steps of:
1. Inserting a tube like instrument into the femoral artery of the patient's body.
2. Using the instrument to guide the rotating body through the femoral artery to the abdominal aorta.
3. Releasing the rotating body inside of the abdominal aorta.
4. Placing a drive unit on the outside of the aorta such that the drive unit is placed in magnetic contact with the rotating body.

The step of placing the drive unit on the outside of the aorta, in any of the embodiments herein, could be performed via an abdominal diaphragm approach entering through the abdomen and further through the thoracic diaphragm of the patient.

Embodiments of a turbine pump have been described. A person skilled in the art realizes that these could be varied within the scope of the appended claims.

The invention claimed is:

1. A heart pump apparatus for assisting the heart of a human patient, the heart pump apparatus comprising
    a turbine pump comprising:
        a rotating body being center axis free, and being adapted to be placed in the blood stream of the patient to provide the heart of the human patient with additional pumping capacity, and having a longitudinal centre in line with and surrounded by the blood stream from inlet to outlet of the rotating body, and
        a plurality of separate blades mounted internally in the rotating body, the blades extending radially internally in the rotating body in relation to the outgoing blood stream, each blade having a first end attached to the rotating body and a second outer free end, which second free end is placed at a distance from the centre of the rotating body,
        the plurality of blades' second outer free ends surrounding the axis free centre of the rotating body, wherein the heart pump apparatus further comprises at least a second rotating body, and wherein the rotating body and the at least second rotating body can be implanted in sequence in the same blood vessel, and wherein one rotating body is adapted to rotate clockwise and the following other rotating body is adapted to rotate counter clockwise, or vice versa.

2. The heart pump apparatus according to claim 1, wherein at least one of the first and second centre axis free rotating bodies are adapted to be placed inside at least one of: the heart of the human patient, the aorta of the human patient, the abdominal aorta of the human patient and the pulmonary artery of the human patient.

3. The heart pump apparatus according to claim 1, wherein the turbine pump further comprises a stator adapted to be placed outside a blood vessel and opposite the rotating body placed in the blood stream.

4. The heart pump apparatus according to claim 3, further comprising an electrically controlled arrangement, the stator being a part of the electrically controlled arrangement, which includes elements for receiving current to increase or decrease a magnetic field created at the stator, at least one of the first and second rotating bodies being adapted to be rotated by the elements provided for such rotation, by creating a magnetic field between the poles of the stator.

5. A heart pump apparatus according to claim 1, comprising a:
    a fitter provided in the blood flow passageway for filtering blood clots, and
    a cleaning device for cleaning the filter, wherein the cleaning device is adapted to move blood clots away from the blood flow passageway, when implanted.

6. The heart pump apparatus according to claim 5, wherein the cleaning device of the turbine pump system is adapted to at last one of: collecting clots that have been cleaned from the filter in a collecting volume, and moving blood clots to a free place inside the patient's body.

7. The heart pump apparatus according to claim 1, wherein said heart pump apparatus further comprises a drive unit for driving at least one of the first and second rotating bodies.

8. The heart pump apparatus according to claim 1, wherein the turbine pump comprises both the rotor, and a stator adapted to be placed outside a blood vessel and opposite the first and second rotating bodies placed in the blood stream, wherein the external rotor is magnetically connected to the rotation body via a magnetic coupling, thus providing rotation of at least one of the first and second rotation bodies when the external rotor is rotated when the apparatus is implanted.

9. The heart pump apparatus according to claim 1, adapted to be fixed to at least one of the sternum, a part of the rib cage comprising one or more ribs, and a part of the vertebral column structure.

10. The heart pump apparatus according to claim 1, comprising confining elements adapted to confine at least one of the first and second rotating bodies in the longitudinal extension of the artery in which it is placed, by at least one of: a magnetic, a mechanical and other confinement.

11. A heart pump apparatus for assisting the heart of a human patient, the heart pump apparatus comprising:
    a turbine pump comprising;
    first and second rotating bodies that are center axis free, and being adapted to be placed in the blood stream of the patient to provide the heart of the human patient with additional pumping capacity, each body having a longitudinal centre in line with and surrounded by the blood stream,
    each body containing a plurality of blades placed internally in the rotating body, the plurality of blades extending radially internally in the rotating body in relation to the outgoing blood stream,
    wherein one of the first and second rotating bodies is adapted to rotate clockwise and the following other of the first and second rotating bodies is adapted to rotate counter clockwise, or vice versa, ensuring laminar blood flow.

12. The heart pump apparatus according to claim 11, comprising a system comprising at least one of:
    an internal energy source for powering implantable energy consuming components of the apparatus, and an internal energy receiver, adapted to be energized non-invasively and wirelessly by an energy transmission device from outside the patient's body, adapted for sending wireless energy to at least one of:
an implantable internal energy source comprised in the system, being chargeable by the energy transferred from the energy transmission device, and
at least one implantable energy consuming component of the system being energised with the wireless energy.

13. The heart pump apparatus according to claim 11, comprising a system further comprising a sensor and/or a measuring device sensing or measuring at least one of:
at least one physical parameter of the patient, and
at least one functional parameter related to the apparatus, comprising at least one of a functional parameter correlated to the transfer of energy for charging the internal energy source, comprised in the system, being chargeable by the energy transferred from the energy transmission device, and a functional parameter related to the apparatus,
wherein the apparatus further comprises a feedback device for sending feedback information from inside the patient's body to at least one of;
an implantable internal control unit,
an external control unit outside of the patients body, and
an external control unit outside of the patients body, via the internal control unit,
an external control unit outside of the patients body, via the internal control unit according to the programming of the internal control unit performed by the external control unit,
wherein the feedback information being related to at least one of the at least one physical parameter of the patient and the at least one functional parameter related to the apparatus.

14. A heart pump apparatus for assisting the heart of a human patient, the heart pump apparatus comprising:
a turbine pump comprising;
first and second rotating bodies that are center axis free, and being adapted to be placed in the blood stream of the patient to provide the heart of the human patient with additional pumping capacity, each body having a longitudinal centre in line with and surrounded by the blood stream,
each body containing a plurality of blades placed internally in the rotating body, the plurality of blades extending radially internally in the rotating body in relation to the outgoing blood stream, comprising a system comprising an internal energy receiver, adapted to be energized non-invasively and wirelessly by an energy transmission device from outside the patient's body, wherein the system further comprising an energy-transmission device comprising a coil placed externally to the human body, the system further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges and/or amplitude of the electrical pulses to vary the power of the transmitted wireless energy, the energy receiver receiving the transmitted wireless energy having a varied power.

15. The heart pump apparatus according to claim 14, comprising a system further comprising a sensor and/or a measuring device sensing or measuring at least one of:
at least one physical parameter of the patient, and
at least one functional parameter related to the apparatus, comprising at least one of; a functional parameter correlated to the transfer of energy for charging the internal energy source, comprised in the system, being chargeable by the energy transferred from the energy transmission device, and a functional parameter related to the apparatus,
wherein the apparatus further comprises a feedback device for sending feedback information from inside the patient's body to at least one of;
an implantable internal control unit,
an external control unit outside of the patients body, and
an external control unit outside of the patients body, via the internal control unit,
an external control unit outside of the patients body, via the internal control unit according to the programming of the internal control unit performed by the external control unit,
wherein the feedback information being related to at least one of; the at least one physical parameter of the patient and the at least one functional parameter related to the apparatus.

16. The heart pump apparatus according to claim 14, wherein the first and second centre axis free rotating bodies are adapted to be placed inside at least one of the heart of the human patient, the aorta of the human patient, the abdominal aorta of the human patient and the pulmonary artery of the human patient.

17. The heart pump apparatus according to claim 14, wherein the turbine pump further comprises a stator adapted to be placed outside a blood vessel and opposite the first and second rotating body placed in the blood stream.

18. The heart pump apparatus according to claim 17, further comprising an electrically controlled arrangement, the stator being a part of the electrically controlled arrangement, which includes elements for receiving current to increase or decrease a magnetic field created at the stator, the first and second rotating bodies being adapted to be rotated by the elements provided for such rotation, by creating a magnetic field between the poles of the stator.

19. The heart pump apparatus according to claim 14, comprising:
a filter provided in the blood flow passageway for filtering blood clots, and
a cleaning device for cleaning the filter, wherein the cleaning device is adapted to move blood clots away from the blood flow passageway, when implanted.

20. The heart pump apparatus according to claim 19, wherein the cleaning device of the turbine pump system is adapted to at last one of: collecting clots that have been cleaned from the filter in a collecting volume, and moving blood clots to a free place inside the patient's body.

21. The heart pump apparatus according to claim 14, wherein said heart pump apparatus further comprises a drive unit for driving at least one of the first and second rotating bodies.

22. The heart pump apparatus according to claim 14, wherein the turbine pump comprises both the rotor, and a stator adapted to be placed outside a blood vessel and opposite the rotating body placed in the blood strewn, wherein the external rotor is magnetically connected to at least one of the first and second rotating body via a magnetic coupling, thus providing rotation of at least one of the first and second rotating body when the external rotor is rotated when the apparatus is implanted.

23. The heart pump apparatus according to claim 14, adapted to be fixed to at least one of: the sternum, a part of the rib cage comprising one or more ribs, and a part of the vertebral column structure.

24. The heart pump apparatus according to claim 14, comprising confining elements adapted to confine at least one of the first and second rotating body in the longitudinal extension of the artery in which it is placed, by at least one of: a magnetic, a mechanical and other confinement.

* * * * *